(12) United States Patent
Hildbrand et al.

(10) Patent No.: US 8,741,920 B2
(45) Date of Patent: Jun. 3, 2014

(54) PROCESS FOR THE MANUFACTURE OF PHARMACEUTICALLY ACTIVE COMPOUNDS

(75) Inventors: Stefan Hildbrand, Gelterkinden (CH); Hans-Juergen Mair, Loerrach (DE); Roumen Nikolaev Radinov, West Caldwell, NJ (US); Yi Ren, Shanghai (CN); James Anderson Wright, Cedar Grove, NJ (US)

(73) Assignee: Hoffmann-La Roche, Inc., Nutley, NJ (US)

( * ) Notice: Subject to any disclaimer, the term of this patent is extended or adjusted under 35 U.S.C. 154(b) by 0 days.

(21) Appl. No.: 13/613,017

(22) Filed: Sep. 13, 2012

(65) Prior Publication Data
US 2013/0005761 A1  Jan. 3, 2013

Related U.S. Application Data

(62) Division of application No. 12/843,908, filed on Jul. 27, 2010, now Pat. No. 8,329,724.

(30) Foreign Application Priority Data

Aug. 3, 2009  (EP) .................................... 09167054
Nov. 5, 2009  (EP) .................................... 09175101

(51) Int. Cl.
*A61K 31/437* (2006.01)

(52) U.S. Cl.
USPC .......................................................... 514/300

(58) Field of Classification Search
USPC .......................................................... 514/300
See application file for complete search history.

(56) References Cited

U.S. PATENT DOCUMENTS

| | | | |
|---|---|---|---|
| 2,234,705 A | 4/1940 | Normington et al. |
| 2,413,258 A | 12/1946 | Soday |
| 3,524,860 A | 8/1970 | Alberstson et al. |
| 4,150,949 A | 4/1979 | Smith |
| 4,301,159 A | 11/1981 | Ogata et al. |
| 4,439,444 A | 3/1984 | Nisato et al. |
| 4,568,649 A | 2/1986 | Bertoglio-Matte |
| 4,595,780 A | 6/1986 | Ogata et al. |
| 4,626,513 A | 12/1986 | Burton et al. |
| 4,634,701 A | 1/1987 | De Vincentiis |
| 4,714,693 A | 12/1987 | Targos |
| 4,727,395 A | 2/1988 | Oda et al. |
| 4,863,945 A | 9/1989 | Friebe et al. |
| 5,120,782 A | 6/1992 | Hubsch et al. |
| 5,124,335 A | 6/1992 | Patchett et al. |
| 5,143,854 A | 9/1992 | Pirrung et al. |
| 5,338,849 A | 8/1994 | Festal et al. |
| 5,360,822 A | 11/1994 | Morino et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |

(Continued)

FOREIGN PATENT DOCUMENTS

| | | |
|---|---|---|
| CA | 2550361 A1 | 7/2005 |
| DE | 2413258 A1 | 10/1975 |

(Continued)

OTHER PUBLICATIONS

Intl Search Report for PCT/EP2010/061079 dated Feb. 17, 2011.
International Search Report mailed on Dec. 17, 2012 for PCT Patent Application No. PCT/EP2011/062207 filed on Jul. 18, 2011, eight pages.

(Continued)

*Primary Examiner* — Niloofar Rahmani
(74) *Attorney, Agent, or Firm* — Morrison & Foerster LLP

(57) ABSTRACT

The present invention relates to a composition comprising the compound of formula (1),

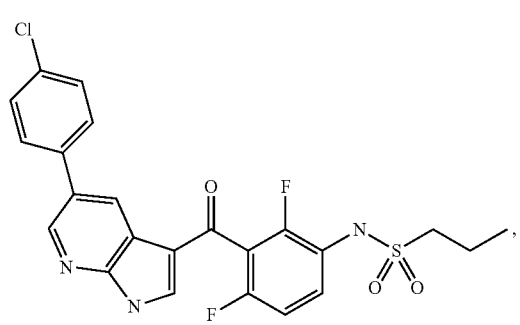

and the compound of formula (B),

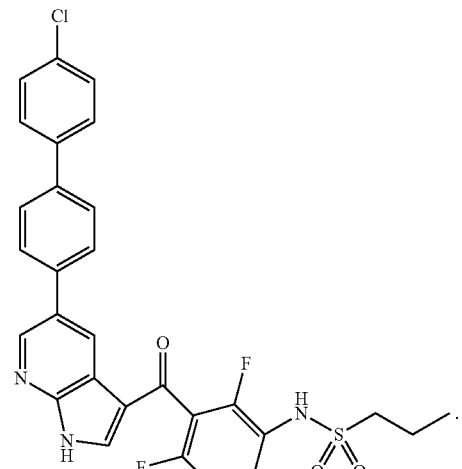

36 Claims, No Drawings

(56) References Cited

U.S. PATENT DOCUMENTS

| | | |
|---|---|---|
| 5,474,935 A | 12/1995 | Chattejee et al. |
| 5,486,525 A | 1/1996 | Summers et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,721,246 A | 2/1998 | Yoshino et al. |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,952,362 A | 9/1999 | Cournoyer et al. |
| 5,958,944 A | 9/1999 | Arita et al. |
| 5,959,098 A | 9/1999 | Goldberg et al. |
| 5,965,452 A | 10/1999 | Kovacs |
| 6,013,440 A | 1/2000 | Lipshutz et al. |
| 6,022,963 A | 2/2000 | McGall et al. |
| 6,025,155 A | 2/2000 | Hadlaczkv et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | Durina |
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossvary |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,348,474 B1 | 2/2002 | Kayakiri et al. |
| 6,350,786 B1 | 2/2002 | Albano et al. |
| 6,451,825 B1 | 9/2002 | Masayoshi et al. |
| 6,476,045 B1 | 11/2002 | Dinnell et al. |
| 6,545,014 B2 | 4/2003 | Verner |
| 6,653,309 B1 | 11/2003 | Saunders et al. |
| 6,673,812 B1 | 1/2004 | Azuma et al. |
| 6,787,534 B2 | 9/2004 | Haneda et al. |
| 6,858,860 B2 | 2/2005 | Hosono et al. |
| 6,897,207 B2 | 5/2005 | Cox et al. |
| 7,109,208 B2 | 9/2006 | Takayama et al. |
| 7,122,318 B2 | 10/2006 | Ono et al. |
| 7,259,165 B2 | 8/2007 | Bernotas et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,893,075 B2 | 2/2011 | Zhang et al. |
| 7,947,706 B2 | 5/2011 | Tabart et al. |
| 7,994,185 B2 | 8/2011 | Rheault |
| 8,067,434 B2 | 11/2011 | Ibrahim et al. |
| 8,067,638 B2 | 11/2011 | Kai et al. |
| 8,143,271 B2 | 3/2012 | Ibrahim et al. |
| 8,198,273 B2 | 6/2012 | Ibrahim et al. |
| 8,329,724 B2 | 12/2012 | Hildbrand et al. |
| 8,415,469 B2 | 4/2013 | Ibrahim et al. |
| 8,470,818 B2 | 6/2013 | Ibrahim et al. |
| 8,530,661 B2 | 9/2013 | Hildbrand et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2002/0028809 A1 | 3/2002 | Imoto et al. |
| 2003/0003004 A1 | 1/2003 | Stones et al. |
| 2003/0219489 A1 | 11/2003 | Curatolo et al. |
| 2004/0002534 A1 | 1/2004 | Lipson et al. |
| 2004/0022534 A1 | 2/2004 | Amano et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2004/0180947 A1 | 9/2004 | Kayakiri et al. |
| 2005/0014942 A1 | 1/2005 | Maruyama et al. |
| 2005/0026792 A1 | 2/2005 | Cartwright |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058339 A1 | 3/2006 | Ibrahim et al. |
| 2006/0058340 A1 | 3/2006 | Ibrahim et al. |
| 2006/0183758 A1 | 8/2006 | Beard et al. |
| 2007/0032519 A1 | 2/2007 | Zhang et al. |
| 2007/0049615 A1 | 3/2007 | Ibrahim et al. |
| 2007/0066641 A1 | 3/2007 | Ibrahim et al. |
| 2007/0072862 A1 | 3/2007 | Dimauro et al. |
| 2007/0218138 A1 | 9/2007 | Bittorf et al. |
| 2007/0287711 A1 | 12/2007 | Arnold et al. |
| 2008/0167338 A1 | 7/2008 | Spevak et al. |
| 2008/0176892 A1 | 7/2008 | Heinrich et al. |
| 2008/0188514 A1 | 8/2008 | Wu et al. |
| 2008/0207700 A1 | 8/2008 | Werz et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0306056 A1 | 12/2009 | Arnold et al. |
| 2010/0310659 A1 | 12/2010 | Desai et al. |
| 2012/0022258 A1 | 1/2012 | Brumsted et al. |
| 2012/0053177 A1 | 3/2012 | Ibrahim et al. |
| 2012/0122860 A1 | 5/2012 | Visor et al. |
| 2012/0245174 A1 | 9/2012 | Ibrahim et al. |
| 2013/0261117 A1 | 10/2013 | Ibrahim et al. |
| 2013/0303534 A1 | 11/2013 | Ibrahim et al. |

FOREIGN PATENT DOCUMENTS

| | | |
|---|---|---|
| EP | 0 148 725 A1 | 7/1985 |
| EP | 0 154 734 A1 | 9/1985 |
| EP | 0 344 603 A1 | 12/1989 |
| EP | 0 465 970 A1 | 1/1992 |
| EP | 0 580 860 A1 | 2/1994 |
| EP | 0 596 406 A1 | 5/1994 |
| EP | 0 870 768 A1 | 10/1998 |
| EP | 0 901 786 A2 | 3/1999 |
| EP | 0 988 863 A2 | 3/2000 |
| EP | 1 057 826 A1 | 12/2000 |
| EP | 1 267 111 A1 | 12/2002 |
| EP | 1 368 001 B1 | 10/2005 |
| EP | 1 749 829 A1 | 2/2007 |

(56) References Cited

FOREIGN PATENT DOCUMENTS

| | | |
|---|---|---|
| FR | 2 264 804 A1 | 10/1975 |
| GB | 1 198 301 A | 7/1970 |
| GB | 1 451 299 A | 9/1976 |
| GB | 2 292 143 A | 2/1996 |
| GB | 2 292 145 A | 2/1996 |
| GB | 2 298 198 A | 8/1996 |
| GB | 2 299 581 A | 10/1996 |
| JP | 6-135946 A | 5/1994 |
| JP | 10-130269 A | 5/1998 |
| JP | 11-284336 A | 10/1999 |
| JP | 2001-278886 A | 10/2001 |
| JP | 2003-73357 A | 3/2003 |
| WO | WO-93/13099 A1 | 7/1993 |
| WO | WO-94/14808 A1 | 7/1994 |
| WO | WO-94/20459 A2 | 9/1994 |
| WO | WO-94/20497 A1 | 9/1994 |
| WO | WO-95/04742 A1 | 2/1995 |
| WO | WO-95/07910 A1 | 3/1995 |
| WO | WO-95/28387 A1 | 10/1995 |
| WO | WO-96/00226 A1 | 1/1996 |
| WO | WO-96/05200 A1 | 2/1996 |
| WO | WO-96/11929 A1 | 4/1996 |
| WO | WO-96/17958 A1 | 6/1996 |
| WO | WO-96/18738 A2 | 6/1996 |
| WO | WO-96/38131 A1 | 12/1996 |
| WO | WO-97/03967 A1 | 2/1997 |
| WO | WO-97/46313 A1 | 12/1997 |
| WO | WO-97/46558 A1 | 12/1997 |
| WO | WO-97/49703 A2 | 12/1997 |
| WO | WO-98/06433 A1 | 2/1998 |
| WO | WO-98/22457 A1 | 5/1998 |
| WO | WO-98/47899 A1 | 10/1998 |
| WO | WO-98/58935 A1 | 12/1998 |
| WO | WO-99/00386 A1 | 1/1999 |
| WO | WO-99/09217 A1 | 2/1999 |
| WO | WO-99/32433 A1 | 7/1999 |
| WO | WO-99/51231 A1 | 10/1999 |
| WO | WO-99/51232 A1 | 10/1999 |
| WO | WO-99/51233 A1 | 10/1999 |
| WO | WO-99/51234 A1 | 10/1999 |
| WO | WO-99/51595 A1 | 10/1999 |
| WO | WO-99/51596 A1 | 10/1999 |
| WO | WO-99/51773 A1 | 10/1999 |
| WO | WO-00/09162 A1 | 2/2000 |
| WO | WO-00/12074 A2 | 3/2000 |
| WO | WO-00/12514 A1 | 3/2000 |
| WO | WO-00/17202 A1 | 3/2000 |
| WO | WO-00/29411 A1 | 5/2000 |
| WO | WO-00/53582 A1 | 9/2000 |
| WO | WO-00/55153 A1 | 9/2000 |
| WO | WO-00/64898 A1 | 11/2000 |
| WO | WO-00/71506 A2 | 11/2000 |
| WO | WO-00/71537 A1 | 11/2000 |
| WO | WO-00/75139 A1 | 12/2000 |
| WO | WO-01/09121 A1 | 2/2001 |
| WO | WO-01/24236 A1 | 4/2001 |
| WO | WO-01/29036 A2 | 4/2001 |
| WO | WO-01/46196 A1 | 6/2001 |
| WO | WO-01/60822 A1 | 8/2001 |
| WO | WO-01/62255 A1 | 8/2001 |
| WO | WO-01/74786 A1 | 10/2001 |
| WO | WO-01/98299 A1 | 12/2001 |
| WO | WO-02/00657 A2 | 1/2002 |
| WO | WO-02/18346 A1 | 3/2002 |
| WO | WO-02/083175 A1 | 10/2002 |
| WO | WO-02/085896 A1 | 10/2002 |
| WO | WO-02/102783 A1 | 12/2002 |
| WO | WO-03/000258 A1 | 1/2003 |
| WO | WO-03/000267 A1 | 1/2003 |
| WO | WO-03/003004 A2 | 1/2003 |
| WO | WO-03/004472 A1 | 1/2003 |
| WO | WO-03/006459 A1 | 1/2003 |
| WO | WO-03/008422 A1 | 1/2003 |
| WO | WO-03/011868 A1 | 2/2003 |
| WO | WO-03/020698 A2 | 3/2003 |
| WO | WO-03/028724 A1 | 4/2003 |
| WO | WO-03/037862 A1 | 5/2003 |
| WO | WO-03/051838 A2 | 6/2003 |
| WO | WO-03/064413 A1 | 8/2003 |
| WO | WO-03/068221 A1 | 8/2003 |
| WO | WO-03/082289 A1 | 10/2003 |
| WO | WO-03/082868 A1 | 10/2003 |
| WO | WO-03/082869 A1 | 10/2003 |
| WO | WO-03/087087 A2 | 10/2003 |
| WO | WO-03/101990 A1 | 12/2003 |
| WO | WO-2004/005283 A1 | 1/2004 |
| WO | WO-2004/009600 A1 | 1/2004 |
| WO | WO-2004/009601 A1 | 1/2004 |
| WO | WO-2004/014369 A1 | 2/2004 |
| WO | WO-2004/016609 A1 | 2/2004 |
| WO | WO-2004/016610 A1 | 2/2004 |
| WO | WO-2004/024895 A2 | 3/2004 |
| WO | WO-2004/052880 A1 | 6/2004 |
| WO | WO-2004/054581 A2 | 7/2004 |
| WO | WO-2004/056830 A1 | 7/2004 |
| WO | WO-2004/065393 A1 | 8/2004 |
| WO | WO-2004/065394 A1 | 8/2004 |
| WO | WO-2004/069138 A2 | 8/2004 |
| WO | WO-2004/074286 A1 | 9/2004 |
| WO | WO-2004/078756 A2 | 9/2004 |
| WO | WO-2004/078923 A2 | 9/2004 |
| WO | WO-2004/101565 A2 | 11/2004 |
| WO | WO-2005/028475 A2 | 3/2005 |
| WO | WO-2005/028624 A2 | 3/2005 |
| WO | WO-2005/030128 A2 | 4/2005 |
| WO | WO-2005/034869 A2 | 4/2005 |
| WO | WO-2005/044181 A2 | 5/2005 |
| WO | WO-2005/058891 A2 | 6/2005 |
| WO | WO-2005/062795 A2 | 7/2005 |
| WO | WO-2005/063746 A1 | 7/2005 |
| WO | WO-2005/063747 A1 | 7/2005 |
| WO | WO-2005/066347 A1 | 7/2005 |
| WO | WO-2005/082367 A1 | 9/2005 |
| WO | WO-2005/085244 A1 | 9/2005 |
| WO | WO-2005/086904 A2 | 9/2005 |
| WO | WO-2005/092896 A1 | 10/2005 |
| WO | WO-2005/095400 A1 | 10/2005 |
| WO | WO-2005/103050 A2 | 11/2005 |
| WO | WO-2005/115363 A2 | 12/2005 |
| WO | WO-2005/115374 A1 | 12/2005 |
| WO | WO-2006/004984 A1 | 1/2006 |
| WO | WO-2006/009755 A2 | 1/2006 |
| WO | WO-2006/009797 A1 | 1/2006 |
| WO | WO-2006/010637 A2 | 2/2006 |
| WO | WO-2006/010637 A3 | 2/2006 |
| WO | WO-2006/015123 A1 | 2/2006 |
| WO | WO-2006/015124 A2 | 2/2006 |
| WO | WO-2006/063167 A1 | 6/2006 |
| WO | WO-2006/114180 A1 | 11/2006 |
| WO | WO-2006/114520 A2 | 11/2006 |
| WO | WO-2006/114520 A3 | 11/2006 |
| WO | WO-2006/127587 A1 | 11/2006 |
| WO | WO-2006/137376 A1 | 12/2006 |
| WO | 2007/002325 | 1/2007 |
| WO | 2007/002433 | 1/2007 |
| WO | 2007002325 * | 1/2007 |
| WO | WO-2007/002325 A1 | 1/2007 |
| WO | WO-2007/002433 A1 | 1/2007 |
| WO | WO-2007/009799 A1 | 1/2007 |
| WO | WO-2007/013896 A2 | 2/2007 |
| WO | WO-2007/013896 A3 | 2/2007 |
| WO | WO-2007/022380 A2 | 2/2007 |
| WO | WO-2007/022380 A3 | 2/2007 |
| WO | WO-2007/106236 A2 | 9/2007 |
| WO | WO-2007/106236 A3 | 9/2007 |
| WO | WO-2008/058341 A1 | 5/2008 |
| WO | WO-2008/064265 A2 | 5/2008 |
| WO | WO-2008/064265 A3 | 5/2008 |
| WO | WO-2008/065417 A1 | 6/2008 |
| WO | WO-2008/079903 A1 | 7/2008 |
| WO | WO-2008/079906 A1 | 7/2008 |
| WO | WO-2008/079909 A1 | 7/2008 |
| WO | WO-2008/138755 A2 | 11/2008 |
| WO | WO-2008/138755 A3 | 11/2008 |

(56) References Cited

FOREIGN PATENT DOCUMENTS

| WO | WO-2009/012283 A1 | 1/2009 |
|---|---|---|
| WO | WO-2009/012791 A1 | 1/2009 |
| WO | 2009/016460 | 2/2009 |
| WO | WO-2009/111277 A1 | 9/2009 |
| WO | WO-2009/111277 A9 | 9/2009 |
| WO | WO-2009/111278 A2 | 9/2009 |
| WO | WO-2009/111278 A3 | 9/2009 |
| WO | WO-2009/111279 A1 | 9/2009 |
| WO | WO-2009/111280 A1 | 9/2009 |
| WO | WO-2010/114928 A2 | 10/2010 |
| WO | WO-2010/114928 A3 | 10/2010 |

OTHER PUBLICATIONS

Written Opinion of the International Searching Authority mailed on Dec. 17, 2012 for PCT Patent Application No. PCT/EP2011/062207 filed on Jul. 18, 2011, ten pages.

Kumar, V. et al. (Dec. 4, 1992). "Synthesis of 7-Azaindole and 7-Azaoxindole Derivatives Through a Palladium-Catalyzed Cross-Coupling Reaction," *Journal of Organic Chemistry* 57(25):6995-6998.

Pillard, C. et al. (May 2008). "Synthesis of 4-,5- and 6-Benzoylated 7-Azaindoles," *Synthesis* 13:2049-2054.

Satoh, M. et al. (Apr. 1987). "Palladium-Catalyzed Cross-Coupling Reaction of (1-Ethoxy-1-alken-2-yl)Boranes with Ortho-Functionalized Iodoarenes. A Novel and Convenient Synthesis of Benzo-Fused Heteroaromatic Compounds," *Synthesis* 373-377.

Whelligan, D.K. et al. (2010, e-pub. Dec. 1, 2009). "Two-Step Synthesis of Aza- and Diazaindoles from Chloroamino-N-Heterocycles Using Ethoxyvinylborolane," *J. Org. Chem.* 75(1):11-15.

Zhao, S-B. et al. (2010, e-pub. Dec. 31, 2009). "New Bimetallic Reactivity in $Pt_2^{II,II}/Pt_2^{IV,IV}$ Transformation Mediated by a Benzene Ring," *Organometallics* 29(4): 998-1003.

Allegretti et al. (2001). "Palladium-Catalysed Functionalisation at 4- and 6-Position of the 7-Azaindole System," *Synlett* 5:609-612.

Al-Obeidi et al. (1998). "Peptide and Peptidomimetic Libraries," *Mol. Biotechnol.* 9(3):205-223.

Alvarez et al. (1999). "Synthesis of 3-Aryl- and 3-Heteroaryl-7-Azaindoles" *Synthesis* 4:615-620.

Anderson et al. (1998). "Cooperative Catalyst Effects in Palladium-Mediated Cyanation Reactions of Aryl Halides and Triflates," *J. Org. Chem.* 63:8224-8228.

Antonini et al. (1982). "Synthesis of 4-Amino-1-β-D-ribofuranosyl-1H-pyrrolo[2,3-b]pyridine (1-Deazatubercidin) as a Potential Antitumor Agent," *J. Med. Chem.* 25:1258-1261.

Arbiser (2007). "Why targeted therapy hasn't worked in advanced cancer," *J. Clin. Invest.* 117(10):2762-2765.

Bartlett et al. (1989). "CAVEAT: A Program to Facilitate the Structure-derived Design of Biologically Active Molecules," in Molecular Recognition: Chemical and Biological Problems, S.M. Roberts (ed.), Royal Society of Chemistry, pp. 182-196.

Barton et al. (1987). "The chemistry of pentavalent organobismuth reagents. Part X. Studies on the phenylation and oxidation of phenols," *Tetrahedron* 43(2):323-332.

Bertolini et al. (1997). "A New Rational Hypothesis for the Pharmacophore of the Active Metabolite of Leflunomide, a Potent Immunosuppressive Drug," *J. Med. Chem.* 40:2011-2016.

Bloom, A. et al. (1939). "The Preparation of 2-Alkylaminobenzimidazoles," *J. Org. Chem.* 14(17):14-19.

Blundell et al. (1988). "Knowledge-Based Protein Modelling and Design," *Eur. J. Biochem.* 172:513-520.

Bohm, H. (1994). "On the Use of LUDI to Search the Fine Chemicals Directory for Ligands of Proteins of Known Three-Dimensional Structure," *J. Comp. Aided Molec. Des.* 8:623-632.

Brenner et al. (1992). "Encoded Combinatorial Chemistry," *PNAS* 89:5381-5383.

Capon et al. (1989). "Designing CD4 Immunoadhesins for AIDS Therapy," *Nature* 337:525-531.

Carell et al. (1995). "New Promise in Combinatorial Chemistry: Synthesis, Characterization, and Screening of Small-Molecule Libraries in Solution," *Chem. Biol.* 3:171-183.

Chabala, J.C. (1995). "Solid-Phase Combinatorial Chemistry and Novel Tagging Methods for Identifying Leads," *Curr. Opin. Biotechnol.* 6:632-639.

Chayer, et al. (2001). "Synthesis of Carboranylpyrroles," *Tetrahedron Lett.* 42(44):7759-7761.

Chappell et al. (2011). "Ras/Raf/MEK/ERK and Pl3K/PTEN/Akt/mTOR Inhibitors: Rationale and Importance to Inhibiting These Pathways in Human Health," *Oncotarget.* 2(3):136-164.

Chou, T. et al. (1984). "Quantitative Analysis of Dose-Effect Relationships: The Combined Effects of Multiple Drugs or Enzyme Inhibitors," *Adv. Enzyme Regul.* 22:27-55.

Chou, T. et al. (1991). "Chemotherapeutic Synergism, Potentiation and Antagonism," Encyclopedia of Human Biology, Academic Press, 2:371-379.

Chou, T. (1991). "The Median-Effect Principle and the Combination Index for Quantitation of Synergism and Antagonism," in Synergism and Antagonism in Chemotherapy, Chou, T. and Rideout, D.C. (eds.), San Diego, CA: Academic Press, Chapter 2, pp. 61-102.

Clark et al. (1995). "PRO_LIGAND: An Approach to De Novo Molecular Design. 1. Application to the Design of Organic Molecules," *J. Comp. Aided Molec. Design* 9:13-32.

Coe et al. (1999). "Solution-Phase Combinatorial Chemistry," *Mol. Divers.* 4(1):31-38.

Colliuod et al. (1993). "Oriented and Covalent Immobilization of Target Molecules to Solid Supports: Synthesis and Application of a Light-Activatable and Thiol-Reactive Cross-Linking Reagent," *Bioconjugate Chem.* 4:528-536.

Colman, P.M. (1994). "Structure-Based Drug Design," *Curr. Opin. Struct. Biol.* 4:868-874.

Coste et al. (1994). "Coupling N-Methylated Amino Acids Using PyBroP and PyCloP Halogenophosphonium Salts: Mechanism and Fields of Application," *J. Org. Chem.* 59:2437-2446.

Crump, M. (2002). "Inhibition of Raf Kinase in the Treatment of Acute Myeloid Leukemia," *Curr. Pharm. Design* 8:(25):2243-2248.

Curtin et al. (1998). "Discovery and Evaluation of a Series of 3-Acylindole Imidazopyridine Platelet-Activating Factor Antagonists," *J. Med. Chem.* 41:74-95.

Cwirla et al. (1990). "Peptides on Phage: A Vast Library of Peptides for Identifying Ligands," *Biochemistry* 87:6378-6382.

Das-Gupta et al. (1941). "Acridine Derivatives, Part IV," *J. Indian Chem. Soc.* 18:25-28.

Dastych et al. (1994). "Stem Cell Factor Induces Mast Cell Adhesion to Fibronectin," *J. Immunol.* 152:213-219.

Demetri (2001). "Targeting c-kit mutations in solid tumors: Scientific rationale and novel therapeutic options," *Seminars in Oncology* 28(5)(Suppl. 17)19-26.

Dewar et al. (2005). "Inhibition of c-fms by Imatinib Expanding the Spectrum of Treatment," *Cell Cycle* 4(7):851-853.

Dolle et al. (1999). "Comprehensive Survey of Combinatorial Library Synthesis: 1998," *J. Comb. Chem.* 1(4):235-282.

Doyle et al. (1979). "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," *J. Org. Chem.* 44(9):1572-1574.

Dube et al. (1999). "Reductive N-Alkylation of Amides, Carbamates and Ureas," *Tetrahedron Lett.* 40:2295-2298.

Dutcher et al. (1951). "Studies of the $C_{11}H_8N_2OS$ Degradation Product of Gliotoxin," *J. Am. Chem. Soc.* 73:4139-4141.

Eklund et al. (2003). "Treatment of rheumatoid arthritis with imatinib mesylate: clinical improvements in three refractory cases," *Annals of Medicine* 35:362-367.

Eliseev et al. (1999). "Dynamic Combinatorial Chemistry: Evolutionary Formation and Screening of Molecular Libraries," *Current Topics in Microbiology & Immunology* 243:159-172.

Enjalbal et al. (2000). "Mass Spectrometry in Combinatorial Chemistry," *Mass Spectrom. Rev.* 19:139-161.

Felder, E.R. (1994). "The Challenge of Preparing and Testing Combinatorial Compound Libraries in the Fast Lane, at the Front End of Drug Development," *Chimia* 48:531-541.

Fischer et al. (2007). "Targeting receptor tyrosine kinase signalling in small cell lung cancer (SCLC): What have we learned so far?," *Cancer Treatment Reviews* 33(4):391-406.

(56) References Cited

OTHER PUBLICATIONS

Franz et al. (1973). "Sulfuranes. X. A Reagent for the Facile Cleavage of Secondary Amides," *J. Am. Chem. Soc.* 95(6):2017-2019.

Friesen et al. (2008). "Hydroxypropyl Methylcellulose Acetate Succinate-Based Spray-Dried Dispersions: An Overview," *Molecular Pharmaceutics* 5(6):1003-1019.

Gallop et al. (1994). "Applications of Combinatorial Technologies to Drug Discovery. 1. Background and Peptide Combinatorial Libraries," *J. Med. Chem.* 37:1233-1251.

Gassman et al. (1973). "Specific ortho substitution of aromatic heterocyclic amines. Conversions of 2-aminopyridines," *J. Am. Chem. Soc.* 95(13):4453-4455.

Ghebre-Sellassie, I. et al. (2003). "Film, Sheet, and Laminates," Chapter 12 in Pharmaceutical Extrusion Technology, Marcel Dekker, Inc., New York, Basel, CRC Press, pp. 225-244.

Girgis, N. et. al. (1989). "The Synthesis of 5-Azaindoles by Substitution-Rearrangement of 7-Azaindoles upon Treatment with Certain Primary Amines," *J. Heterocyclic Chem.* 26:317-325.

Gordon et al. (1972). "Detection of Peroxides and Their Removal," in The Chemist's Companion: A Handbook of Practical Data, Techniques, and References, p. 437.

Gordon et al. (1994). "Applications of Combinatorial Technologies to Drug Discovery. 2. Combinatorial Organic Synthesis, Library Screening Strategies, and Future Directions," *J. Med. Chem.* 37:1385-1401.

Gravert et al. (1997). "Synthesis on Soluble Polymers: New Reactions and the Construction of Small Molecules," *Curr. Opin. Chem. Biol.* 1:107-113.

Guida, W. (1994). "Software for Structure-Based Drug Design," *Curr. Opin. Struct. Biol.* 4:777-781.

Hands et al. (Jul. 1996). "A Convenient Method for the Preparation of 5-, 6- and 7-Azaindoles and Their Derivatives," *Synthesis* 877-882.

Hayashi et al. (1984). "Dichloro[1,1'-bis(diphenylphosphino)ferrocene]palladium-(II): An Effective Catalyst for Cross-Coupling of Secondary and Primary Alkyl Grignard and Alkylzinc Reagents with Organic Halides," *J. Am. Chem. Soc.* 106:158-163.

Haydock et al. (1984). "Analogues of clofibrate and clobuzarit containing fluorine in the side chains," *Eur. J. Med. Chem.* 19:205-214.

Heacock et al. (1960). "Orientation and Relative Reaction Rate Factors in Aromatic Substitution by the Benzenesulfonimido Radical," *J. Am. Chem. Soc.* 82:3460-3463.

Heinrich, M.C. et al. (2002). "Inhibition of KIT Tyrosine Kinase Activity: A Novel Molecular Approach to the Treatment of KIT-Positive Malignancies," *J. Clin. Oncol.* 20(6):1692-1703.

Hoffmann, R.V. (1981/1990). "*m*-Trifluoromethylbenzenesulfonyl Chloride," *Organic Syntheses Coll.* vol. 7, p. 508; vol. 60, p. 121.

Houghten et al. (1991). "Generation and Use of Synthetic Peptide Combinatorial Libraries for Basic Research and Drug Discovery," *Nature* 354:84-86.

Houghten, R. (2000). "Parallel Array and Mixture-Based Synthetic Combinatorial Chemistry: Tools for the Next Millennium," *Annu. Rev. Pharmacol. Toxicol.* 40:273-282.

Houghten, R. (1993). "Peptide Libraries: Criteria and Trends," *Trends Genet.* 9:235-239.

Ibrahim et al. (2007). Caplus, pp. 11300, two pages.

Jarugula et al. (1997). "Nonlinear pharmacokinetics of 5-fluorouracil in rats," *J. Pharm. Sci.* 86(6):756-757.

Jones et al. (1984). "Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl][4-[2-(1-piperidinyl)ethoxy]-phenyl]methanone Hydrochloride (LY156758), a Remarkably Effective Estrogen Antagonist with Only Minimal Intrinsic Estrogenicity," *J. Med. Chem.* 27:1057-1066.

Jones, R.J. (1997). "Biology and treatment of chronic myeloid leukemia," *Curr. Opin. Onc.* 9:3-7.

Joseph-McCarthy, D. (1999). "Computational Approaches to Structure-Based Ligand Design," *Pharmacology & Therapeutics* 84:179-191.

Katritzky et al. (2003). "Regiospecific C-Acylation of Pyrroles and Indoles Using N-Acylbenzotriazoles," *J. Org. Chem.* 68:5720-5723.

Kim et al. (2000). "A Merger of Rational Drug Design and Combinatorial Chemistry: Development and Application of Peptide Secondary Structure Mimetics," *Comb. Chem. High Throughput Screen.* 3:167-183.

Kim et al. (2002). "Preparation of 2-anilino-4-indolylpyrimidines as tyrosine kinase inhibitors," 138:55974 (abstract).

Kirkpatrick et al. (1999). "Structure-Based Drug Design: Combinatorial Chemistry and Molecular Modeling," *Comb. Chem. High Throughput Screen.* 2:211-221.

Kitamura et al. (2003). "Synthesis of Quinolines and 2H-Dihydropyrroles by Nucleophilic Substitution at the Nitrogen Atom of Oxime Derivatives," *Synthesis* 15:2415-2426.

Kline et al. (1986). "Studies by $^1$H Nuclear Magnetic Resonance and Distance Geometry of the Solution Conformation of the x-Amylase Inhibitor Tendamistat," *J. Mol. Biol.* 189:377-382.

Komoyira, S. et al. (2004). "Design, synthesis and biological activity of amidinobicyclic compounds (derivatives of DX-9065a) as a factor Xa inhibitors: SAR study of S1 and aryl binding sites," *Bioorg. Med. Chem.* 12:2099.

Konno et al. (2006). "Influence of Different Polymers on the Crystallization Tendency of Molecularly Dispersed Amorphous Felodipine," *J. Pharm. Sci.* 95(12):2692-2705.

Kundu et al. (1999). "Combinatorial Chemistry: Polymer Supported Synthesis of Peptide and Non-Peptide Libraries," in *Progress in Drug Research*, Jucker, E. (ed.), Springer Verlag AG, 53:89-156.

Kuntz et al. (1994). "Structure-Based Molecular Design," *Acc. Chem. Res.* 27:117-123.

Lam et al. (1991). "A New Type of Synthetic Peptide Library for Identifying Ligand-Binding Activity," *Nature* 354:82-84.

Langham et al. (1941). "Metalation and Halogen-Metal Interconversion Reactions of Some Halogenated Phenyl Ethers," *J. Am. Chem. Soc.* 63:545-549.

Lebl et al. (1995). "One-Bead-One-Structure Combinatorial Libraries," *Biopolymers* 37:177-198.

Leuner, C. et al. (2000). "Improving drug solubility for oral delivery using solid dispersions," *Eur. J. Pharm. Biopharm.* 50:47-60.

Lipinski et al. (1997). "Experimental and Computational Approaches to Estimate Solubility and Permeability in Drug Discovery and Development Settings," *Adv. Drug Deliv. Rev.* 23:3-25.

Liu et al. (2006). "Sorafenib blocks the RAF/MEK/ERK pathway, inhibits tumor angiogenesis, and induces tumor cell apoptosis in hepatocellular carcinoma model PLC/PRF/5," *Cancer Res.* 66:11852-11858.

Ma et al. (2000). "Indolinone Derivatives Inhibit Constitutively Activated KIT Mutants and Kill Neoplastic Mast Cells," *J. Invest. Dermatol.* 114:392-394.

Ma et al. (2002). "The c-kit mutation causing human mastocytosis is resistant to ST1571 and other KIT kinase inhibitors; kinases with enzymatic site mutations show different inhibitor sensitivity profiles than wild-type kinase and those with regulatory-type mutations," *Blood* 99:1741-1744.

Madden, et al. (1994). "Synthetic Combinatorial Libraries: Views on Techniques and Their Application," *Perspectives in Drug Discovery and Design* 2:269-285.

Madhusudan et al. (2004). "Tyrosine kinase inhibitors in cancer therapy," *Clin. Biochem.* 37(7):618-635.

Markiewicz et al. (2000). "Synthetic Oligonucleotide Combinatorial Libraries and Their Applications," *Il Farmaco* 55:174-177.

Martin, Y. (1991). "Computer-Assisted Rational Drug Design," *Methods Enzymol.* 203:587-613.

Matsumoto et al. (1999). "Physical properties of solid molecular dispersions of indomethacin with poly(vinyl)pyrrolidinone and poly(vinylpyrrolidinone-co-vinyl-acetate) in relation to indomethacin crystallization," *Pharm. Res.* 16(11):1722-1728.

Mazeas et al. (1999). "Synthesis of New Melatoninergic Ligands Including Azaindole Moiety," *Heterocycles* 50(2):1065-1080.

McPherson, A. (1990). "Current Approaches to Macromolecular Crystallization," *Eur. J. Biochem.* 189:1-23.

Merour et al. (2001). "Synthesis and Reactivity of 7-Azaindoles (1H-Pyrrolo[2,3-b]pyridine)," *Current Organic Chemistry* 5:471-506.

Merritt, A.T. (1998). "Solution Phase Combinatorial Chemistry," *Comb. Chem. High Throughput Screen.* 1(2):57-72.

(56) References Cited

OTHER PUBLICATIONS

Meula Pomeda et al. (2002). "Efecto de codisolventes y dispersiones solidas de polivinilpirrolidona K-30 en la solubilidad del tiabendazol," 86 VI Congreso SEFIG y 3$^{as}$ Jornadas TF, pp. 85-87 (with English translation of Introduction).

Miller et al. (1994). "FLOG: A System to Select 'Quasi-Flexible' Ligands Complementary to a Receptor of Known Three-Dimensional Structure," *J. Comp.-Aided Mol. Des*. 8:153-174.

Minakata et al. (1992). "Functionalization of 1H-Pyrrolo[2,3-b]pyridine." *Bull. Chem. Soc. Japan* 65(11):2992-2997.

Minakata et al. (Jul. 1992). "Regioselective Functionalization of 1H-Pyrrolo[2,3-b]pyridine via its N-Oxide," *Synthesis* pp. 661-663.

Miyaura et al. (1995). "Palladium-Catalyzed Cross-Coupling Reactions of Organoboron Compounds," *Chem. Rev*. 95:2457-2483.

Mokhtari et al. (2010). "Potential utility of small tyrosine kinase inhibitors in the treatment of diabetes," *Clin. Sci*. 118(4):241-247.

Mol et al. (2004). "Structural Basis for the Autoinhibition and STI-571 Inhibition of c-Kit Tyrosine Kinase," *J. Biol. Chem*. 279:31655-31663.

Nagafuji et al. (1996). "A General Synthesis of Pyrroles and Fused Pyrrole Systems from Ketones and Amino Acids," *J. Org. Chem*. 61:4999-5003.

Nahm et al. (1981). "N-Methoxy-N-Methylamides as Effective Acylating Agents," *Tetrahedron Lett*. 22(39):3815-3818.

Nakai et al. (1988). "New Potent Antagonists of Leuokotrienes $C_4$ and $D_4$. 1. Synthesis and Structure-Activity Relationships," *J. Med. Chem*. 31:84-91.

Neidle et al. (1991). "Molecular Modeling to Study DNA Intercalation by Anti-Tumor Drugs," *Methods Enzymol*. 203:433-458.

Ng et al. (1995). "Engineering Protein-Lipid Interactions: Targeting of Histidine-Tagged Proteins to Metal-Chelating Lipid Monolayers," *Langmuir* 11:4048-4055.

Olah et al. (1984). "Synthetic Methods and Reactions: Part 209. Improved Preparation of Aldehydes and Ketones from N,N-Dimethylamides and Grignard Reagents," *Synthesis* pp. 228-230.

Ottoni et al. (1998). "Efficient and Simple Methods for the Introduction of the Sulfonyl, Acyl and Alkyl Protecting Groups on the Nitrogen of Indole and its Derivatives," *Tetrahedron* 54:13915-13928.

Owicki et al. (1997). "Application of Fluorescence Polarization Assays in High-Throughput Screening," *Genetic Engineering News* 17:28.

Panitumumab PiCCA Study (Panitumumab in Combination with Cisplatin/Gemcitabine) (2012). National Cancer Institute at the National Institutes of Health, located at http://clinicaltrials.gov/ct2/show/NCT01320254, last visited on Dec. 16, 2013, 5 pages.

Parker et al. (2000). "Development of High Throughput Screening Assays Using Fluorescence Polarization: Nuclear Receptor-Ligand-Binding and Kinase/Phosphatase Assays," *J. Biomol. Screen*. 5:77-88.

Patani et al. (1996). "Bioisosterism: A rational approach in drug design," *Chem. Rev*. 96:3147-3176.

Perrin, D.M. (2000). "Nucleic Acids for Recognition and Catalysis: Landmarks, Limitations, and Looking to the Future," *Comb. Chem. High Throughput Screen*. 3:243-269.

Pflugrath et al. (1986). "Crystal Structure Determination, Refinement and the Molecular Model of the α-Amylase Inhibitor Hoe-467A," *J. Mol. Biol*. 189:383-386.

Pierce et al. (1942). "Local anaesthetics. I. Beta-Monoalkylaminoethyl Esters of Alkoxybenzoic Acids," *J. Am. Chem. Soc*. 64:1691-1694.

Plunkett et al. (1995). "A Silicon-Based Linker for Traceless Solid-Phase Synthesis," *J. Org. Chem*. 60:6006-6007.

Remington. (1995). "Preformulation," Chapter 83 in *Remington: The Science and Practice of Pharmacy, Remington's Pharmaceutical Sciences*, 19th ed., Mack Publishing Co., Easton, PA, vol. 2, pp. 1457-1462.

Robison et al. (1955). "7-Azaindole. I. Synthesis and Conversion to 7-Azatryptophan and Other Derivatives," *J. Am. Chem. Soc*. 77:457-460.

Rodan, G. et al. (2000). "Therapeutic Approaches to Bone Diseases," *Science* 289:1508-1514.

Saify et al. (1994). "Synthesis of some 7-azaindole derivatives: their cytotoxicity and antibacterial activity," *Pakistan Journal of Scientific and Industrial Research* 37(10):439-441.

Saiki, R. (1990). "Amplification of Genomic DNA," in PCR Protocols: A Guide to Methods and Applications, Academic Press, Inc.: San Diego, CA 2:13-20.

Sathornsumetee et al. (2006). "AAL881, a novel small molecule inhibitor of RAF and vascular endothelial growth factor receptor activities, blocks the growth of malignant glioma," *Cancer Res*. 66:8722-8730.

Sawada et al. (2001). "4-(Benzoylindolizinyl)butyric acids: Novel nonsteroidal inhibitors of steroid 5α-reductase. III," *Chem. Pharm. Bull*. 49(7):799-813.

Schiemann et al. (1943). "p-Fluorobenzoic Acid," *Org. Synth. Coll*. vol. 2, 299, 4 total pages.

Schneller et al. (1980). "Synthesis of 4-Amino-1H-Pyrrolo[2,3-b]pyridine (1,7-Dideazaadenine) and 1H-Pyrrolo[2,3-b]pyridin-4-ol (1,7-Dideazahypoxanthine)," *J. Org. Chem*. 45:4045-4048.

Schweizer et al. (1999). "Combinatorial Synthesis of Carbohydrates," *Curr. Opin. Chem. Biol*. 3(3):291-298.

Shah et al. (2006). "Analytical Techniques for Quantification of Amorphous/Crystalline Phases in Pharmaceutical Solids," *J. Pharm. Sci*. 95(8):1641-1665.

Shan et al. (1997). "Prodrug strategies based on intramolecular cyclization reactions," *J. Pharm. Sci*. 86(7):765-767.

Song et al. (2002). "Isomerism of Bis(7-azaindolyl)methane." *Org. Lett*. 4:23:4049-4052 and Supporting information pp. 1-15.

Sorafenib Tosylate. (2012). National Cancer Institute at the National Institutes of Health, located at <http://www.cancer.gov/cancertopics/druginfo/sorafenibtosylate>, last visited on Dec. 16, 2013, two pages.

Su et al. (1960). "Synthesis of Bromo-substituted Indoxyl Esters for Cytochemical Demonstration of Enzyme Activity," *J. Am. Chem. Soc*. 82:1187-1189.

Sun, C. (1999). "Recent Advances in Liquid-Phase Combinatorial Chemistry," *Comb. Chem. High Throughput Screen*. 2:299-318.

Sun, C. (1999). "Design, Synthesis and Evalutions of Substituted 3-[(3- or 4-Carboxyethylpyrrol-2-yl)methylidenyl]indolin-2-ones as Inhibitors of VEGF, PGF, and PDGF Receptor Tyrosine Kinases," *J. Med. Chem*. 42:5120-5130.

Tanno et al. (2004). "Evaluation of Hypromellose Acetate Succinate (HPMCAS) as a Carrier in Solid Dispersions," *Drug Dev. Ind. Pharm*. 30(1):9-17.

Thibault et al. (2003). "Concise and Efficient Synthesis of 4-Fluoro-1H-pyrrolo[2,3-b]pyridine," *Org. Lett*. 5:5023-5025.

Thomas et al. (2001). "Light-Emitting Carbazole Derivatives: Potential Electroluminescent Materials," *J. Am. Chem. Soc*. 123:9404-9411.

Toste et al. (1995). "A Versatile Procedure for the Preparation of Aryl Thiocyanates Using N-Thiocyanatosuccinimide (NTS)," *Synth. Commun*. 25(8):1277-1286.

Uritskaya et al. (1973). Azaindole derivatives. XLIII. Synthesis of 1-acetyl-4-methyl-7-azatryptamine, STN Accession No. 1974:27133; Document No. 80:27133; Abstract of Khimiya Geterotsiklichenskikh Soedinenii 10:1370-1373.

Vachon et al. (1997). "The influence of microencapsulation using Eudragit RS100 on the hydrolysis kinetics of acetylsalicylic acid," *J. Microencapsulation* 14:281-301.

Vandelli et al. (1993). "Analysis of release data in the evaluation of the physical state of progesterone in matrix systems," *J. Microencapsulation* 10(1):55-65.

Weber, P. (1991). "Physical Principles of Protein Crystallization," *Adv. Protein Chem*. 41:1-36.

Wells et al. (2009). "Targeting the RET Pathway in Thyroid Cancer," *Clin. Cancer Res*. 15(23):7119-7123.

Wendt et al. (2004). "Identification of novel binding interactions in the development of potent, selective 2-naphthamidine inhibitors of urokinase. Synthesis, structural analysis, and SAR of N-phenyl amide 6-substitution," *J. Med. Chem*. 47(2):303-324.

Wessjohann, L. (2000). "Synthesis of Natural-Product-Based Compound Libraries," *Curr. Opin. Chem. Biol*. 4:303-309.

(56) References Cited

OTHER PUBLICATIONS

Yakhontov et al. (1965). "Derivatives of 7-azaindole. XV. Electrophilic substitution of 4-methyl-7-azaindole and its derivatives." Zhurnal Obshchei Khimii 1(11):2032-2040. (English abstract only).

Yang, et al. (1992). "Synthesis of Some 5-Substituted Indoles," *Heterocycles* 34:1169-1175.

Yeung et at. (2002). "Friedel-Crafts acylation of indoles in acidic imidazolium chloroaluminate ionic liquid at room temperature," *Tetrahedron Lett.* 43(33):5793-5795.

Zanon et al. (2003). "Copper-Catalyzed Domino Halide Exchange-Cyanation of Aryl Bromides," *J. Am. Chem. Soc.* 125:2890-2891.

Zhang et al. (2002). "An effective procedure for the acylation of azaindoles at C-3," *J. Org. Chem.* 67(17):6226-6227 and p. S1-S30.

\* cited by examiner

PROCESS FOR THE MANUFACTURE OF PHARMACEUTICALLY ACTIVE COMPOUNDS

PRIORITY TO RELATED APPLICATION(S)

This application is a divisional application of U.S. application Ser. No. 12/843,908, filed Jul. 27, 2010, and claims the benefit of European Patent Application No. 09167054.7, filed Aug. 3, 2009, and European Patent Application No. 09175101.6, filed Nov. 5, 2009, both of which are hereby incorporated by reference in their entirety.

FIELD OF THE INVENTION

The present invention is related to synthesis routes to obtain the compound propane-1-sulfonic acid {3-[5-(4-chloro-phenyl)-1H-pyrrolo[2,3-b]pyridine-3-carbonyl]-2,4-difluoro-phenyl}-amide (formula 1).

Formula (1)

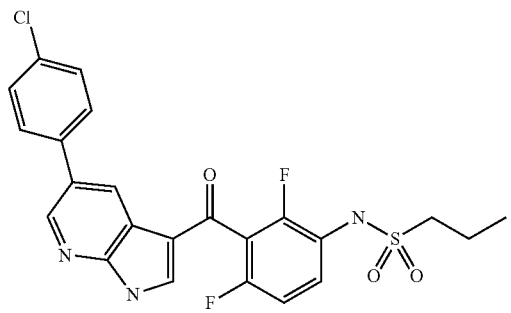

The synthesis of the compound of formula (1) has been described before in WO 2007002433 and WO 2007002325.

However, the known synthesis routes may not be readily adapted for use on an industrial scale.

SUMMARY OF THE INVENTION

The present invention relates in part to a process for the manufacture of the compound of formula (1), (1)

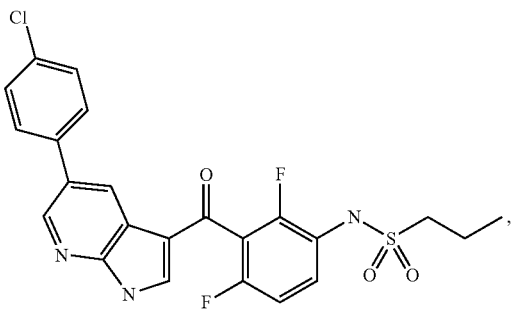

comprising the steps of reacting the compound of formula (5), (5)

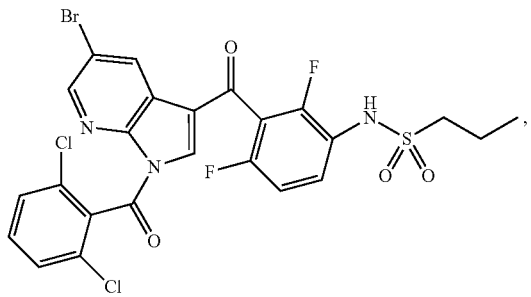

with 4-chlorophenylboronic acid in the presence of a palladium catalyst to produce the compound of formula (6), (6)

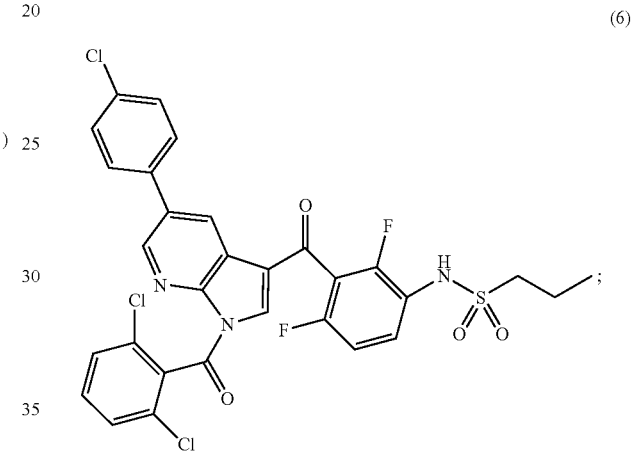

and cleaving the 2,6-dichlorobenzamide group in said compound of formula (6) to produce the compound of formula (1).

The present invention also relates in part to a compound of formula (A), (A)

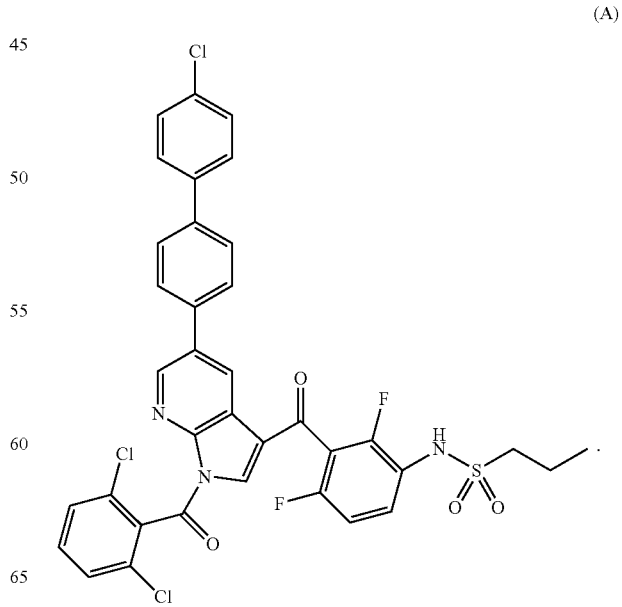

The present invention further relates in part to a compound of formula (B)

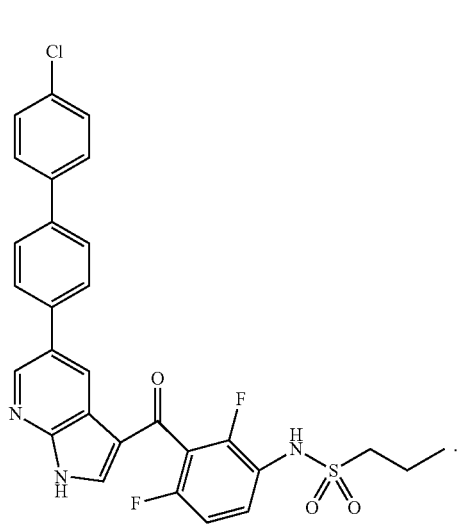

(B)

In addition, the present invention relates to a composition comprising the compound of formula (1) and the compound of formula (B).

The present invention also relates to an analytical method for the detection of whether the process as described above has been used in the manufacture of the compound of formula (1), said method comprising obtaining a sample from a medicament primarily containing the compound of formula (1) as active ingredient, and applying a suitable analytical method in order to detect whether said sample contains the compound of formula (B), wherein the presence of any amount of the compound of formula (B) indicates that the process has been used.

The present invention further relates to a process for the manufacture of compound (I),

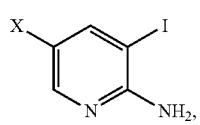

(I)

comprising the steps of:
aa) reacting the compound of formula (II),

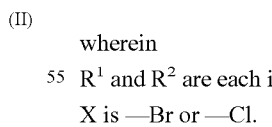

(II)

with the compound of formula (III),

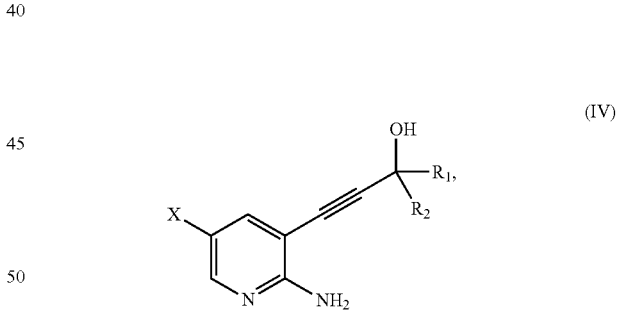

(III)

in the presence of a catalyst, copper(I)iodide and a base, to produce the compound of formula (IV),

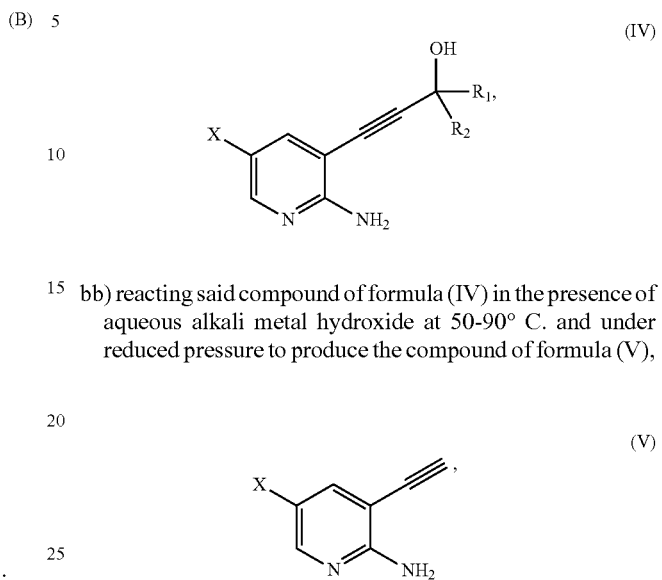

(IV)

bb) reacting said compound of formula (IV) in the presence of aqueous alkali metal hydroxide at 50-90° C. and under reduced pressure to produce the compound of formula (V), (V)

and
cc) reacting said compound of formula (V) in the presence of aqueous alkali metal hydroxide or a strong base to produce the compound of formula (I);
wherein
R$^1$ and R$^2$ are each independently a C1-C4 alkyl, and
X is —Br or —Cl.

In addition, the present invention relates to a compound of formula (IV), (IV)

wherein
R$^1$ and R$^2$ are each independently a C1-C4 alkyl, and
X is —Br or —Cl.

DETAILED DESCRIPTION OF THE INVENTION

The present invention provides new and improved synthesis routes for the compound of formula (1), which employ reaction conditions which are particularly amenable to being carried out on an industrial scale.

According to the present invention, there is provided a process for the manufacture of the compound of formula (1), (1)

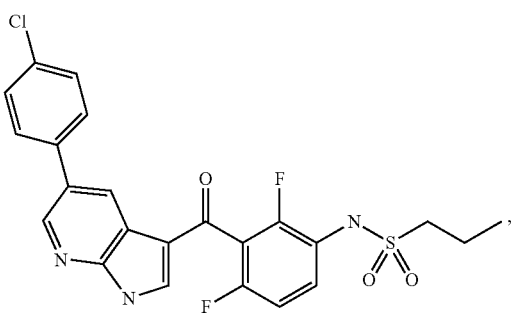

comprising the steps of reacting the compound of formula (5), (5)

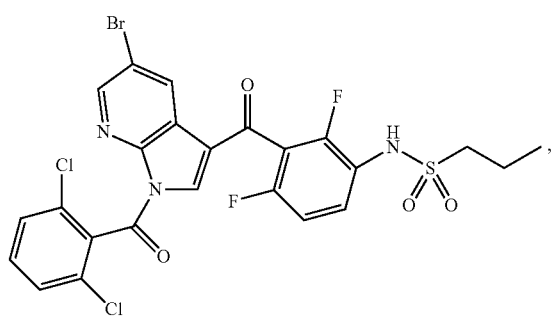

with 4-chlorophenylboronic acid (5a, scheme 1) in the presence of a palladium catalyst to produce the compound of formula (6), (6)

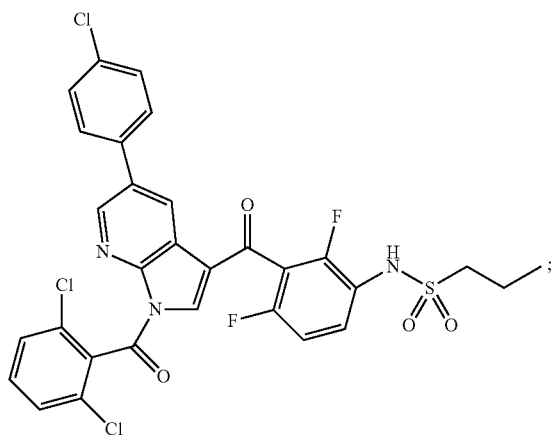

and
cleaving the 2,6-dichlorobenzamide group in said compound of formula (6), for example using ammonia, to produce the compound of formula (1).

The process according to the present invention efficiently uses starting materials, avoids formation of high quantities of undesirable by-products, provides high throughput and good product yields and can safely be carried out in large scale production. It is also less expensive, and, due to the efficient use of starting materials, environmentally friendlier than processes disclosed in the prior art.

The term "palladium catalyst" as used herein means any suitable palladium (Pd) catalyst, preferably bis(triphenylphosphin)palladium(II)dichloride ($(PPh_3)_2PdCl_2$) and Pd on charcoal. Preferably, the amount of $(PPh_3)_2PdCl_2$ is about 0.0025 equivalents with respect to compound of formula (5).

The compound of formula (5) can be obtained according to methods known to the person of skill in the art of organic chemistry. In a particularly preferred embodiment according to the present invention, the compound of formula (5) is obtained by reacting the compound of formula (2), (2)

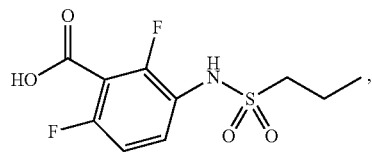

with a suitable activating agent (e.g., oxalylchloride ($(COCl)_2$)) to produce the corresponding acid chloride, then reacting said acid chloride with 5-Bromo-7-azaindole (formula 3) and a suitable coupling agent (e.g., aluminium trichloride) to produce the compound of formula (4)

(4)

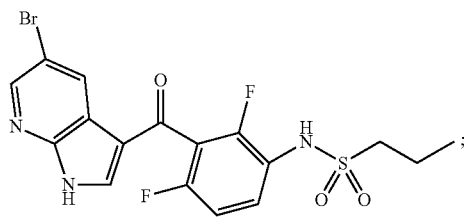

and reacting said compound of formula (4) with 2,6-dichlorobenzoylchloride under conditions suitable to produce the compound of formula (5).

In another particularly preferred embodiment according to the present invention there is provided the process for the manufacture of the compound of formula (1), wherein
a) the compound of formula (2)

(2)

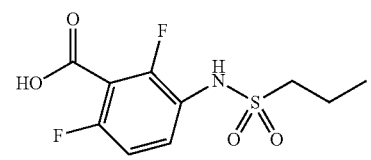

is reacted in a suitable solvent (e.g., methylenechloride ($CH_2Cl_2$)) with a suitable activating agent (e.g., Vilsmeier's salt prepared in situ from oxalylchloride ($(COCl)_2$ and N,N-Dimethylformamide (DMF)) to produce the corresponding acid chloride, then reacting said acid chloride with 5-bromo-7-azaindole (formula 3) in the presence of a suitable activating agent (e.g., aluminium trichloride) to produce the com pound of formula (4), (4)

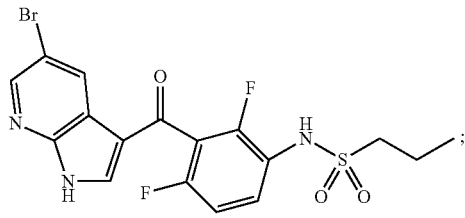

b) reacting said compound of formula (4) i with 2,6-dichlorobenzoylchloride in the presence of a suitable base (e. g. n-Tripropylamine (n-Pr₃N)) and suitable catalyst (e.g. N,N-Dimethylaminopyridine (DMAP)) to produce the compound of formula (5), (5)

c) reacting said compound of formula (5) with 4-chlorophenylboronic acid in the presence of a suitable palladium catalyst (e.g., $(PPh_3)_2PdCl_2$) to produce the compound of formula (6)

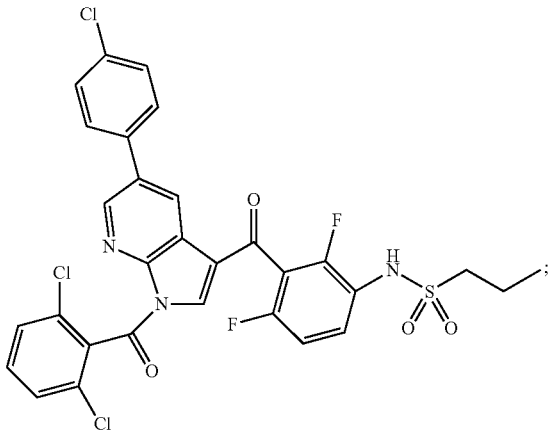

and d) reacting said compound of formula (6) with ammonia ($NH_3$) or a primary or secondary amine (e.g. dimethylamine) in an alcohol (methanol or ethanol) solution diluted with a polar aprotic solvent like DMA to produce the compound of formula (1).

In a preferred embodiment according to the present invention, the above-mentioned reaction step c) is carried out in a 2 phase reaction mixture comprising a non-polar aprotic solvent such as anisole or toluene and aqueous sodium or potassium carbonate ($Na_2CO_3$, $K_2CO_3$).

The compounds (4), (5) and (6) are novel and each form an embodiment of the present invention.

The process according to the present invention can be summarized according to the following reaction scheme (scheme 1) wherein, unless explicitly otherwise stated, all abbreviations and expressions have the meanings well known to the person of skill in the art of organic chemistry. All reaction partners and auxiliary agents (like i.e. catalysts, solvents) are commercially available.

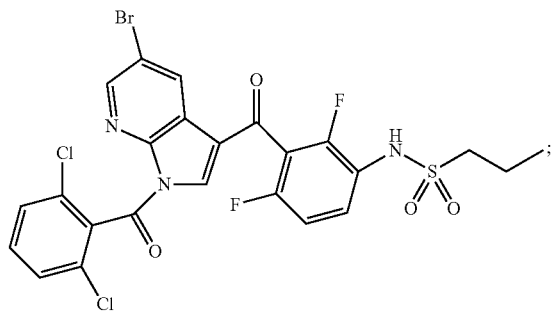

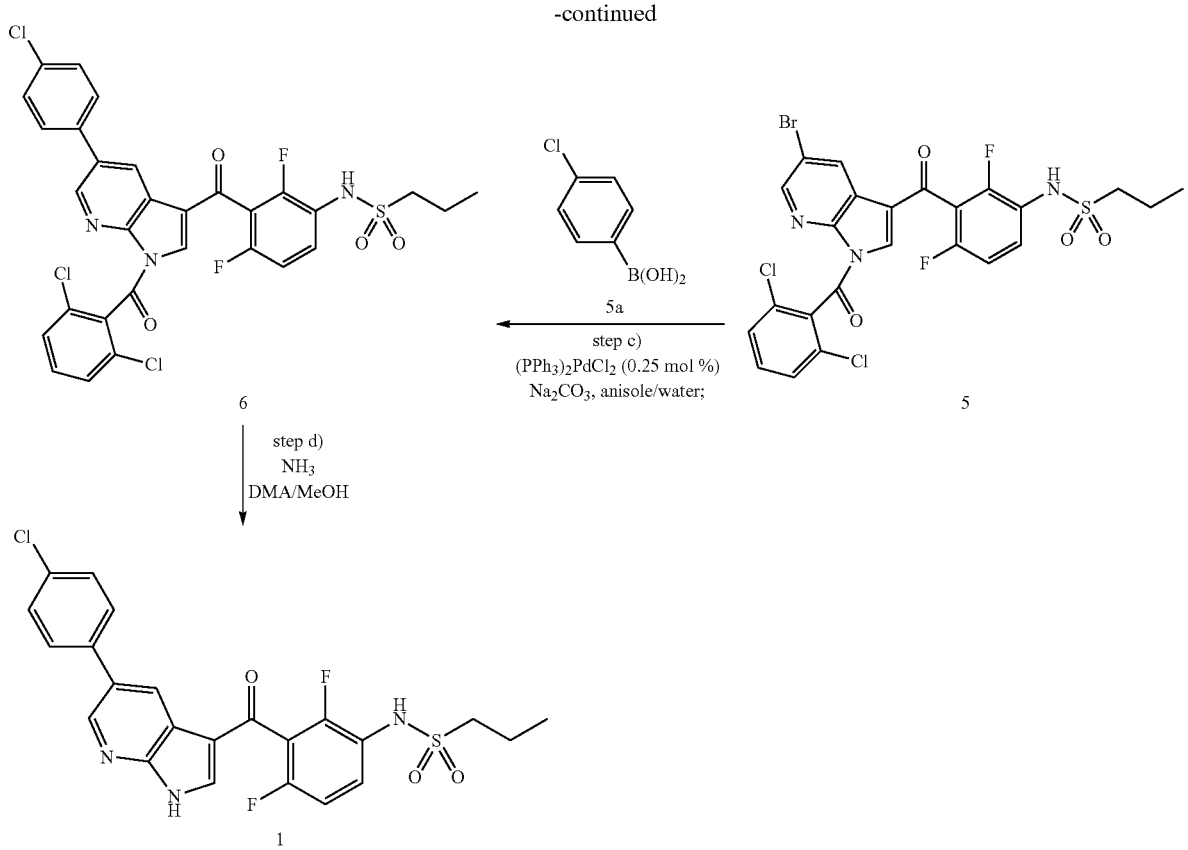

According to the present invention, the first reaction under step a) is the formation of an acid chloride of the carboxylic acid of formula (2). The reaction can be carried out employing a suspension of the compound of formula (2) in suitable medium, e.g., methylenechloride ($CH_2Cl_2$) containing catalytic amounts of DMF, to which a solution of oxalylchloride (($COCl)_2$) in $CH_2Cl_2$ is slowly added. The addition is typically carried out at room temperature (RT) and the reaction mixture is further stirred at RT until reaction completion (ca 6h). The next reaction is a Friedel-Crafts-Acylation. The freshly obtained solution of acid chloride is added into a cooled (T=−12 to 5° C., preferably 0-5° C.) suspension of $AlCl_3$ and 5-Bromo-7-azaindole (3) in $CH_2Cl_2$. The reaction mixture is allowed to heat up till RT due to released heat of the exothermic reaction and stirred for about 8h to complete the reaction. The work-up and isolation procedure involves pouring of the reaction mixture into iced water, followed by extractive work-up and crystallization of the compound of formula (4) from THF/methylenchloride/heptane. The compound of formula (4) can be further purified by washing with i.e. heptane.

Reaction step b) starts with the preparation of a suspension of the compound of formula (4) in a suitable aprotic solvent (e.g., toluene). Subsequently dimethylaminopyridine (DMAP), n-tripropylamine and 2,6-dichlorobenzoylchloride are added at RT. The reaction mixture is stirred for about 60 minutes. After completion of the reaction an aqueous work-up is performed. Subsequently the toluene is slowly evaporated from the organic solution, leading to the crystallization of the compound of formula (5) which can finally be isolated and further purified through additional washing with e.g., cooled toluene.

Reaction step c) is a Pd-catalyzed Suzuki-coupling reaction of the compound of formula (5) with 4-chlorophenylboronic acid (5a). The reaction starts with the preparation of a suspension of 4-chlorophenylboronic acid (5a) and the compound of formula (5) in an aprotic solvent, such as anisole, to which an aqueous solution of $Na_2CO_3$ is added. The reaction mixture is heated slowly up to a temperature of about 85° C. During heating the Pd-catalyst is added at a temperature between RT and around 70° C. Any suitable Pd-catalyst can be used, with bis(triphenylphosphin) palladium(II)dichloride (($PPh_3)_2PdCl_2$) being especially preferred. The reaction mixture is stirred for about 120 minutes at a temperature of about 85° C. to complete the reaction. The hot bi-phasic reaction mixture is filtered to remove potentially precipitated Pd. After aqueous work-up the organic (anisole) phase is concentrated by evaporation, diluted with methanol and cooled down to about 0° C. in order to initiate crystallization of the compound of formula (6). The precipitate is isolated, washed several times with cooled methanol and subsequently dried in vacuum. If needed the compound of formula (6) can be further purified by re-crystallization from Toluene.

Reaction step d) is the removal of the 2,6-dichlorobenzamide protection group. The reaction is carried out in a suspension/solution of the compound of formula (6) in DMA/methanol (about 1:1-2:1) by addition of about 3-7 equivalents of a saturated ammonia solution ($NH_3$ in Methanol) at RT. The reaction mixture is stirred at about 55° C. until the protection group is entirely cleaved (about 10 h). The resulting solution is diluted with methanol and subsequently the ammonia is removed via azeotropic distillation under reduced pressure. The residue is diluted with methanol and cooled to RT in order to initiate crystallization of the compound of formula (1) which can then be isolated from the reaction mixture by filtration. The compound of formula (1) can be further purified by washing with e.g., methanol.

In another embodiment of the present invention there are identified specific compounds (compounds (A) and (B) as specified below) which are by-products of the present synthesis method.

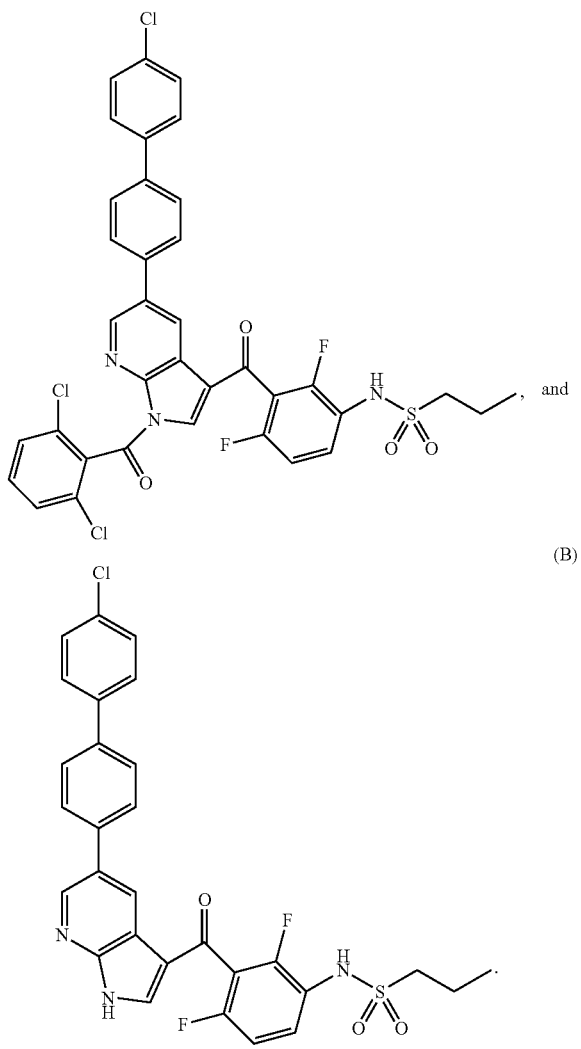

The compound of formula (A) may be formed during the reaction of the compound of formula (5) with 4-Chlorophenylboronic acid (step c), scheme 1. The compound of formula (B) is the de-protected form of formula (A) as obtained during reaction step d) as defined above (see also scheme 1). These compounds, in particular the compound of formula (B) can serve as characteristic fingerprints for the use of the present process.

Trace amounts of the compound of formula (B) are typically found in the final product (formula (1)) as a pharmaceutically acceptable impurity in an amount of less than 0.30%, and usually in an amount of from about 0.02% to about 0.15%, as identified by HPLC, provided said compound of formula (1) had been synthesized according to the present method. Therefore, while the impurity/trace amounts of the compound of formula (B) will not affect the pharmacological- or toxicity profile of any potential future medicament or pharmaceutical preparation containing the compound of formula (1), said compound may nevertheless serve as a fingerprint in order to detect whether the present process has been used to manufacture the compound of formula (1). The presence of the compound of formula (B) will therefore allow for an unambiguous identification as to whether the present process has been used in the manufacture of the compound of formula (1).

The compounds of formulas (A) and (B), in particular the compound of formula (B), may be detected in amounts of from about 0.02% to about 0.15% by weight in a composition which otherwise contains >99% by weight of the compound of formula (1) formed using the process according to the present invention, and even following conventional purification methods known to the person of skill in the art. Therefore, trace amounts of the compound of formula (B) may even be detectable in pharmaceutical preparations containing the compound of formula (1) when obtained according to the present process. The compounds of formula (A) and (B) show the following NMR signals:

Compound A:
1H-NMR (500 MHz, d6-DMSO): δ0.99 (t, J=7.5 Hz, 3H), 1.72-1.82 (m, 2H), 3.15-3.21 (m, 2H), 7.37 (t, J=9.0 Hz, 1H), 7.52-7.58 (m, 2H), 7.65-7.74 (m, 4H), 7.76-7.85 (m, 4H), 7.87-7.92 (m, 2H), 8.58 (br. s, 1H), 8.82 (d, J=2.5 Hz, 1H), 8.90 (br. s, 1H), 9.85 (br. s, 1H).

Compound B:
1H-NMR (600 MHz, d6-DMSO): δ0.97 (t, J=7.5 Hz, 3H), 1.70-1.80 (m, 2H), 3.10-3.15 (m, 2H), 7.29 (t, J=8.7 Hz, 1H), 7.54-7.63 (m, 3H), 7.78-7.82 (m, 2H), 7.83-7.90 (m, 4H), 8.25 (s, 1H), 8.70 (br. s, 1H), 8.79 (d, J=1.8 Hz, 1H), 9.78 (br. s, 1H), 13.02 (br. s, 1H).

Therefore, as a further embodiment according to the present invention, there are provided the compounds of formulae (A) and (B) as such.

In yet another embodiment the present invention provides an analytical method for detecting whether the process according to the present invention has been used, characterized in that detectable levels of the compounds of formula (A) and/or (B) as disclosed herein are generally present in any commercial pharmaceutical preparation comprising primarily the compound of formula (1) prepared employing the synthetic process disclosed herein. Preferably the analytical method is used to detect the compound of formula (B). Any suitable analytical method known to the Organic Chemist may be applied, such as for example IR-spectroscopy, NMR-spectroscopy, Mass Spectrometry (MS) or High Performance Liquid Chromatography (HPLC). More preferably the analytical method is based on High Performance Liquid Chromatography (HPLC), which may optionally be combined with a second analytical method such as for example MS (HPLC-MS).

An aspect of the present invention is an analytical method for the detection of whether the process described above has been used in the manufacture of the compound of formula (1), said method comprising obtaining a sample from a medicament primarily containing the compound of formula (1) as active ingredient, and applying a suitable analytical method in order to detect whether said sample contains the compound of formula (B), wherein the presence of any amount of the compound of formula (B) indicates that said process has been used.

The compound of formula (1) shows potential as an active pharmaceutical ingredient, as inter alia described in WO 2007002433 and WO 2007002325. Consequently, in a further embodiment of the present invention, there is provided a pharmaceutical preparation comprising the compound of formula (1) together with detectable amounts of at least compound of formula (B). More particularly there is provided a composition comprising the compound of formula (1) in an amount greater than 99% by weight and the compound of formula (B) in amounts from about 0.01% to about 0.15% by weight. Said composition may be further processed with pharmaceutically acceptable adjuvants to give any kind of pharmaceutical preparations as inter alia described in WO 2007002433 and WO 2007002325.

The starting materials, solvents, catalysts and auxiliary reagents used in the method according to the present invention (see i.e. scheme 1) are commercially available. However, when produced on a large industrial scale, there remains a need to also obtain large amounts of starting materials in good quality and high yields.

Consequently, according to the present invention, there are also provided improved methods of making azaindole derivatives which are halogenated at their 5-position, in particular 5-bromo-7-azaindole ((3), CAS 183208-35-7) and 5-chloro-7-azaindole (CAS 866546-07-8). 5-Bromo-7-azaindole is a useful starting material in the above-mentioned process according to scheme 1.

Consequently, in a further embodiment according to the present invention there is provided a process for the manufacture of compound (I),

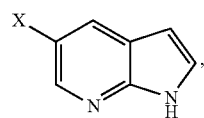
(I)

comprising the steps of:
aa) reacting the compound of formula (II),

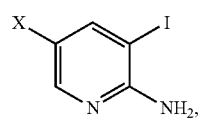
(II)

with the compound of formula (III),

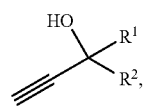
(III)

in the presence of a catalyst, copper(I)iodide and a base, to produce the compound of formula (IV),

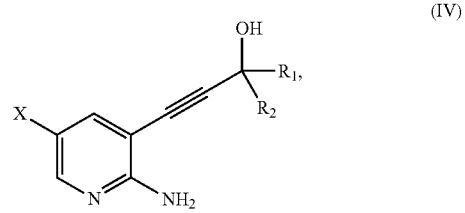
(IV)

bb) reacting said compound of formula (IV) in the presence of aqueous alkali metal hydroxide at 50-90° C. and under reduced pressure to produce the compound of formula (V)

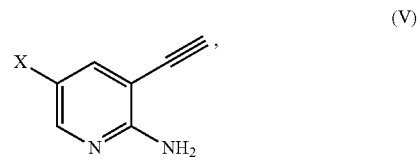
(V)

and
cc) reacting said compound of formula (V) in the presence of aqueous alkali metal hydroxide or a strong base to produce the compound of formula (I);
wherein
$R^1$ and $R^2$ are each independently selected from a C1-C4 alkyl, and
X is —Br or —Cl.

In one particularly preferred embodiment according to the present invention, the above process aa) to cc) is carried out with X being —Br.

In another particularly preferred embodiment according to the present invention, the above process aa) to cc) is carried out with X being —Cl.

In still another preferred embodiment according to the present invention $R_1$ and $R_2$ are both methyl.

The synthesis of compounds of formula (I) as described above is a sequential process. After each reaction described in steps aa) to cc), aqueous work-up procedures are applied and the formed intermediate product is optionally being isolated. In an alternative setup it is also possible to carry out the reaction steps bb) and cc) almost simultaneously. This means the conversion of compound (V) into compound (I) starts as soon as compound (V) is formed, and before the reaction to obtain compound (V) (step bb)) is terminated. Therefore, the two reaction steps bb) and cc) may run under the same reaction conditions. Consequently, no work-up of compound (V) prior to its further reaction to compound (I) is required according to this alternative method.

Therefore, in yet another embodiment there is provided a method to obtain the compound of formula (I) directly from formula (IV) without the need to apply an aqueous work-up on the stage of the compound of formula (V). This can be achieved by adding to the compound of formula (IV), dissolved in an approximately 1:1 (w/w) mixture of water and N-methylpyrrolidone (NMP), 5 to 10 equivalents of aqueous sodium hydroxide at about 75 to about 85° C. while applying a pressure of about 350 mbar, followed by stirring at about 75 to about 85° C. and under reduced pressure (<400 mbar) for 15 to 20 hours. During the entire reaction time distilled acetone/water is continuously replaced by water. The termination of the reaction can be monitored by taking a sample out of the reaction mixture after 15 to 20 hours and analyzing said sample with HPLC. A specific procedure for this reaction is disclosed in Example 7b.

The term "C1-C4 alkyl" as used herein means a linear or branched saturated hydrocarbon, such as for example methyl, ethyl, propyl, i-propyl, n-butyl, 2-butyl, tert-butyl, with methyl being especially preferred.

The term "alkali metal hydroxide" as used herein means sodium-, lithium- or potassium hydroxide, with lithium- and sodium hydroxide being especially preferred.

The term "reduced pressure" as used herein means <500 mbar, preferably <400 mbar.

The term "catalyst" as used herein in step aa) means any Pd(II)- or Pd(0)-catalyst usually used in this type of Sonogashira reaction. Examples of such catalysts are $Pd(PPh_3)_4$, $PdCl_2(PPh_3)_2$, $Pd(OAc)_2$, $Pd_2(dba)_3$ with bis-(triphenylphosphine)-palladium(II)-dichloride ($PdCl_2(PPh_3)_2$) being especially preferred.

The term "base" as used herein in step aa) means weak bases as for example N-methylmorpholine or trialkyl-amines, with triethylamine being especially preferred.

The term "strong base" as used herein in step cc) means alkali metal alcoholates, preferably potassium tert.-butylate.

In an embodiment of the invention, step bb) is carried out under reduced pressure below 100 mbar.

In an embodiment, the catalyst in step aa) is $PdCl_2(PPh_3)_2$ and the alkali metal hydroxide in step bb) is lithium- or sodium hydroxide.

In an embodiment, the compound of formula (IV) is dissolved in a mixture of water and N-methylpyrrolidone, and is reacted in the presence of aqueous sodium hydroxide at about 75 to about 85° C. and under reduced pressure for 15 to 20 hours to give directly the compound of formula (I) without the need to apply an aqueous work-up of the compound of formula (V).

In a particularly preferred embodiment according to the present invention, the above-mentioned reaction step aa) is carried out in the presence of bis-(triphenylphosphine)-palladium(II)-dichloride, copper(I)iodide and triethylamine, the reaction step bb) is carried out with aqueous lithium- or sodium hydroxide and the reaction step cc) is carried out in the presence of potassium tert.-butylate or aqueous sodium hydroxide. The elimination of acetone (step bb) and subsequent ring formation of step cc) are preferably carried out in N-methylpyrrolidone or in a mixture of N-methylpyrrolidone and water as solvent.

The process according to the reaction steps aa) to cc) is preferably carried out according to the specific conditions and parameters given in Example 7a) or b). Consequently, the specific process according to Example 7a) or b) form each another preferred embodiment according to the present invention.

The compounds of formula (II) can be obtained for example by iodination of the corresponding 5-halogenated 2-amino-pyridines. Among the many iodination conditions known to the skilled in the art a mixture of iodine and periodic acid proved to be especially suitable for the mentioned transformation.

The above described synthesis route via the compound of formula (IV) is a novel, alternative method for the production of the otherwise well known compounds of formula (I), in particular the 5-bromo-7-azaindole (3). A particular advantage of this process is the use of the intermediate compound of formula (IV) which can be easily purified and isolated from the reaction mixture. In addition, the use of compound (IV) avoids the release of environmentally hazardous Si by-products upon cyclization, which are formed if the corresponding trimethylsilyl-ethynyl derivative is used, which is usually known for this type of reaction (Sonogashira reaction) as inter alia described in WO 2009/016460 and US 2006/0183758.

The compounds of formula (IV) are thus valuable and novel intermediates in the above-described synthesis to obtain 5-halogenated 7-azaindoles (I). Therefore, in yet another embodiment according to the present invention there is provided the compounds of formula (IV) as such.

The present invention is now illustrated by the following accompanying working examples. In some examples, the term "In-process control" is used. This term means that a sample is taken from the reaction mixture while the process is running, and said sample is being analyzed by standard techniques known to the skilled person, preferably by HPLC, in order to detect the degree of conversion of starting material into product.

EXAMPLES

Example 1

(Step a))

| | Formation of Carboxylic Acid Chloride (step a) 1) according to scheme 1) |
|---|---|
| 55.8 g | Sulfonamide Acid (2) was placed into a dried 1$^{st}$ reaction vessel kept under nitrogen atmosphere, to which |
| 280 mL | methylenchloride were added. Then |
| 619 µL | DMF were added to the obtained suspension and the resulting mixture was kept at a temperature between 18-22° C. Then, |
| 25.4 g | oxalylchloride were dissolved in |
| 66 mL | methylenchloride, and this solution was slowly added over approximately 30 minutes to the above-mentioned suspension whereby the temperature of said suspension was kept between 18-22° C. The formation of $CO_2$ and CO could be observed during said addition. The reaction mixture was then further stirred for about 4 to 6 hours and further kept at a temperature between 18-22° C. until the suspension almost entirely turned into a solution and no gas formation could be observed any more. |
| | Friedel-Crafts-Acylation |

In parallel to the above described formation of the acid-chloride, a 2$^{nd}$ reaction vessel was prepared, wherein

| Formation of Carboxylic Acid Chloride (step a) 1) according to scheme 1) |   |
|---:|---|
| 106.7 g | aluminiumtrichloride were mixed together with |
| 266 mL | methylenchloride to produce a suspension which was then cooled down to about −12 to 2° C. In parallel, a suspension of |
| 39.4 g | 5-bromo-7-azaindole in |
| 66 mL | methylenchloride was prepared in a $3^{rd}$ dried reaction vessel under nitrogen atmosphere. Said bromoazaindole suspension was added to said aluminiumtrichloride suspension over approximately 30 minutes and at a temperature between −12 to 2° C. |
|  | The obtained suspension was immediately further reacted by addition of the acid-chloride solution as obtained according to the procedure described above over approximately 30 minutes, whereby the reaction mixture was allowed to warm up to about 20-25° C. using the spontaneous heat release observed upon addition of the said acid chloride solution. After addition of the acid-chloride solution, the reaction mixture was further stirred over approximately 8 to 10 hours; whereby the mixture was kept at a temperature between 20-25° C. During this time a separation into 2 phases was observed. Meanwhile, a $4^{th}$ reaction vessel was prepared, containing |
| 400 ml | water which was cooled to a temperature between 0-5° C. The two phase reaction mixture as obtained according to the preceding steps was added slowly, over approximately 30 minutes, to said cooled water into said $4^{th}$ reaction vessel whereby the resulting mixture was kept at a temperature between 0-20° C. This resulted in an exothermic reaction and precipitation of the compound of formula (4) from the resulting biphasic reaction mixture. Methylene chloride was widely removed by distillation under reduced pressure from the heterogeneous mixture. Then the aqueous suspension of the compound of formula (4) was diluted with methylene chloride and THF. A clear biphasic mixture was obtained by heating the reaction mixture to about 50° C. After phase separation the organic phase was washed twice with 400 ml semi-saturated brine at about 50° C. The organic phase was concentrated under reduced pressure at about 50° C. to a volume of about 400 ml whereby crystallization of the compound of formula (4) started. |
| 600 ml | Heptane was added within about 30 min at about 50° C. The resulting suspension was cooled in about 3-5 h to ca. 0° C. After stirring for at least one additional hour at ca. 0° C. to complete the crystallization, the suspension was filtered and the wet precipitate was washed two times with |
| 120 mL | n-heptane. The wet product was dried in vacuum and at a temperature between 50-60° C. |

Yield: 85 g (=90%) light beige colored, crystalline azaindole (4).

Example 2

Step b

| Formation of compound (5) |   |
|---:|---|
| 45.8 g | of the compound (4) as obtained according to Example 1 were suspended in |
| 600 ml | toluene. Water as contained in the suspension was removed at a temperature between 60-80° C. and under reduced pressure of 450-400 mbar. Subsequently, |
| 200 ml | toluene were newly added and the suspension was cooled to 20-25° C. Then, a solution of |
| 1.22 g | dimethylaminopyridine in |
| 20 ml | toluene was added, prior to the addition of |
| 15.8 g | n-tripropylamine. Subsequently, |
| 22.0 g | 2,6-dichlorobenzoylchloride were slowly added via a dropping funnel over approximately 15 minutes while the mixture was kept between 20 and 25° C. |

The reaction mixture was stirred for about 1-2 hours at a temperature between 20-25 °C., whereby the color of the mixture turned into brown.

The brownish reaction mixture as obtained by the last step above, was diluted with

| | | |
|---|---|---|
| 275 | ml | water and subsequently with |
| 29.6 | g | hydrochloric acid (37%). The resulting two phase mixture was heated to 65-70° C. The two phases were allowed to separate after about 10 minutes. The toluene phase was washed at a temperature between 65 and 70° C., first with |
| 300 | ml | of an aqueous solution containing 10% sodium hydrogencarbonate, and then with |
| 300 | ml | water. The organic (toluene) phase was concentrated by evaporation at temperatures between 55 and 60° C. and at reduced pressure (200-80 mbar) to a volume of about 200 ml. During this procedure the crude product (5) precipitated due to crystallization. The resulting suspension was then slowly cooled down (within about 5 h) to −5 to 0° C. and further stirred at that temperature for 1 h. The crude product was separated by filtration, washed twice with |
| 30 | ml | toluene (0° C.), and was subsequently dried at 50-55° C. and 26-13 mbar. |

Yield: 57 g (90%) of compound of formula (5).

Example 3

Step c

| | | |
|---|---|---|
| | | Formation of compound (6), Suzuki-Coupling |
| 23.16 | g | 4-Chlorphenylboronic acid (5a) were mixed with |
| 85.00 | g | of compound (5) as obtained according to Example 2 in a dried 1$^{st}$ reaction vessel under nitrogen atmosphere. To the resulting suspension were further added |
| 395 | ml | anisole. The suspension was kept at room temperature (20-25° C.) and mixed with a solution of |
| 57.08 | g | sodium carbonate in |
| 337 | ml | water. The reaction mixture was then heated to a temperature of 70 +/− 2° C. At this temperature, |
| 0.236 | g | bis-(triphenylphosphin)-palladium(II)-dichloride together with |
| 110 | ml | anisole were added to the reaction mixture, which was subsequently slowly (within about 60 minutes) heated up to a temperature between 80-88° C. (Heating Temperature outside did not exceed 110° C.) and stirred for about 2 h. Towards the end of the reaction the formation of a clear two phase reaction mixture with a dark red upper (organic) phase was obtained. After completion of the reaction, the reaction mixture was cooled down to 60-80° C. and transferred via a filter into a 2nd reaction vessel. The 1st reaction vessel and the filter were washed with |
| 110 | ml | warm anisole which was added to the 2$^{nd}$ reaction vessel. The obtained two phases were separated and the organic phase was washed at 60-80° C., first with |
| 375 | ml | 0.1N sulfuric acid containing 10% (w/w) sodium sulfate, and subsequently with |
| 375 | ml | water. During the last extraction, reversal of the two phases was observed. The organic phase was now the lower phase. In order to obtain complete phase separation, the last extraction was carried out at a temperature of at least 70° C. The obtained orange-yellow solution was concentrated at reduced pressure to about 225 mL (+/−10%), while the temperature of the solution was kept between 60-80° C. Subsequently, the resulting suspension was cooled to about 60° C. Then, over a period of about 30 minutes, |
| 628 | ml | methanol were continuously added. Subsequently, the suspension was slowly (within about 4 hours) cooled to 0° C. (+/−2° C.), and stirred for another 3 hours at that temperature until complete crystallization of the product of formula (6) occurred. The suspension was separated by filtration, and the wet solid residue was washed two times with |
| 112 | ml | cold methanol. The wet chlorophenylbenzamide (6) was dried in a rotary evaporator under reduced pressure and at a water bath temperature between 70-80° C. |

Yield: 74-76 g (82-85%) almost colorless, crystalline Chlorophenylbenzamide (6). The product can be optionally re-crystallized from toluene for further purification.

1H-NMR (400 MHz, CDCl3): δ ppm 1.09 (t, J=7.5 Hz, 3H), 1.86-1.99 (m, 2H), 3.10-3.19 (m, 2H), 6.53 (s, 1H), 7.11 (dt, J=8.6, 1.5 Hz, 1H), 7.39-7.49 (m, 5H), 7.50-7.59 (m, 2H), 7.79 (td, J=9.0, 5.6 Hz, 1H), 8.32 (br. s, 1H), 8.43 (br. s, 1H), 8.84 (d, J=2.3 Hz, 1H).

Example 4

Step d

| Formation of compound (1) |   |
|---|---|
| 70.0 g | Chlorphenylbenzamide (6), |
| 175 ml | DMA and |
| 88 ml | methanol were placed into a dried reaction vessel under nitrogen atmosphere. The resulting suspension was kept at 20-25° C., and mixed with |
| 48.0 g | of a solution of ammonia in methanol (15%). The autoclave was then closed and the reaction mixture heated to 50-55° C., which resulted in the formation of a clear solution. The temperature was maintained while stirring the reaction mixture for about 10-20 hours. Subsequently, the clear solution was transferred into a double jacket reaction vessel, and further diluted with |
| 254 ml | methanol. The reaction mixture was then concentrated to its original volume under reduced pressure and (600-500 mbar) at a jacket-temperature of maximum 60° C. Subsequently, |
| 508 ml | methanol were newly added slowly over a period of about 20-30 minutes, whereby the temperature of the reaction mixture was kept between 45-55° C. The resulting suspension was slowly cooled down (within about 2 hours) to 20° C. (±3° C.) and subsequently was further stirred for at least 1 hour prior to separation of the solid reaction product (1) by filtration. The filter cake was washed two times with |
| 120 mL | methanol. The wet product was dried in rotary evaporator under reduced pressure and while applying a water bath temperature of 50 to 60° C. |

Yield: 49 g (95%) of the white, crystalline compound formula (1).

1H-NMR (600 MHz, CDCl3): δ ppm 1.07 (t, J=7.5 Hz, 3H), 1.84-1.98 (m, 2H), 3.07-3.17 (m, 2H), 6.41 (s, 1H), 7.06 (dt, J=8.6 Hz, 1.5 Hz, 1H), 7.46-7.51 (m, 2H), 7.60-7.64 (m, 2H), 7.70 (td, J=9.0, 5.5 Hz, 1H), 7.73 (d, J=2.7 Hz, 1H), 8.65 (d, J=2.2 Hz, 1H), 8.88 (d, J=1.9 Hz, 1H), 9.55 (br. s, 1H).

Purity: ≥99% (m/m, HPLC); Palladium content ≤5 ppm; compound (B): about 0.1%

Example 5

Preparation of 2-amino-5-bromo-3-iodopyridine (IIa)

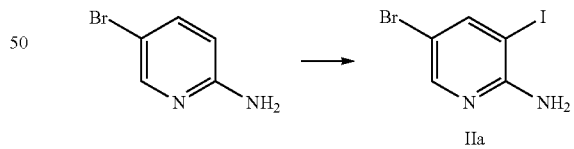

IIa

| In a 1000 mL double-jacket reactor (under a nitrogen atmosphere) | |
|---|---|
| 38.28 g | iodine is suspended in |
| 21 g | acetic acid and |
| 62 g | acetonitrile. To the brown mixture is added at 20 to 40° C. |
| 14.6 g | sulfuric acid 96%. The addition is strongly exothermic. The dropping funnel is rinsed with |

| | In a 1000 mL double-jacket reactor (under a nitrogen atmosphere) |
|---|---|
| 20 g | water. The resulting mixture is heated with a jacket temperature of 90° C. When the temperature of the mixture is 70° C., the mixture is treated within 3 to 6 minutes with |
| 45.20 g | periodic acid (50% in water). The addition is endothermic. The funnel is rinsed with |
| 10 g | water. The solution is then treated at 65 to 75° C. within 5 to 10 minutes with a previously prepared solution of |
| 58.00 g | 2-amino-5-bromopyridine in |
| 67 g | acetonitrile and |
| 31.5 g | acetic acid. The dropping funnel is rinsed with |
| 15 g | acetonitrile. The resulting solution is heated to 77 to 82° C. and stirred under slightly reflux conditions for 3 to 4 hours (approx. 90° C. jacket temperature). In-process control (proposed target value: <2.0% starting material). Upon complete conversion the mixture is immediately cooled down and treated at 60 to 70° C. drop wise with |
| 66 g | sodium hydrogen sulfite (38-40% in water). Immediately after the addition, the mixture is diluted at 60 to 70° C. within 30 to 60 minutes with |
| 360 g | water. The mixture is then treated at 60 to 70° C. within 50 to 90 minutes with approximately |
| ~202 g | sodium hydroxide 28% to adjust the pH to 7.3 to 7.6. When the desired pH is reached the suspension is stirred at 60 to 70° C. for 30 to 60 minutes. The suspension is cooled to 20 to 25° C. within 2 to 5 hours and then stirred at this temperature for 2 to 5 hours. The crystals are filtered off and washed in two portions with a mixture of |
| 270 g | water and |
| 23 g | acetonitrile. The wet crystals (approx. 120 g) are dried at 40 to 50° C./<30 mbar until constant weight. |

Yield: 90.5 g of slightly brownish crystals with an assay of 95.0% (m/m). This corresponds to a corrected yield of 86%.

Example 6 a) Preparation of 4-(2-Amino-5-bromo-pyridin-3-yl)-2-methyl-but-3-Yn-2-Ol.

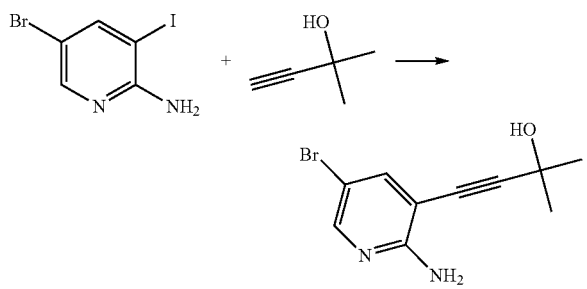

A suspension of 2-amino-5-bromo-3-iodopyridine (10.0 g, 33.5 mmol), bis-(triphenyl-phosphine)-palladium(II)-dichloride (117 mg, 0.17 mmol), copper(I)iodide (79 mg, 0.41 mmol) and triethylamine (6.1 mL, 43.5 mmol) in dichloromethane (40 mL) was treated at 23 to 30° C. within 1 to 2 hours with a solution of 1,1-dimethyl-2-propyn-1-ol (3.70 g, 44 mmol) in dichloromethane (10 mL) and the resulting mixture was stirred at 25° C. for 3 hours. The mixture was diluted with dichloromethane (20 mL) and washed with water (2×50 mL). The organic phase was then treated with 1 M HCl (80 mL). The layers were separated and the organic layer was extracted with 1 M HCl (20 mL). The combined product containing aqueous layers were washed with dichloromethane (2×10 mL). The pH of the aqueous layer was adjusted to pH 7-9 by the drop wise addition of sodium hydroxide solution (28% in water, 18 g). The resulting suspension was stirred at 20° C. for 2 hours and the crystals were then filtered off and washed with water (2×20 mL). The wet crystals were dried at 50° C./<30 mbar affording 6.99 g (82%) of 4-(2-amino-5-bromo-pyridin-3-yl)-2-methyl-but-3-yn-2-ol as a melted mass with a purity of 99.5% (HPLC, area%). $^1$H NMR (400 MHz, CDCl$_3$): δ ppm 1.63 (s, 6H); 4.0 (br., 3H); 7.59 (d, J=2.4, 1H); 8.03 (d, J=2.4, 1H).

b) Alternative Preparation of 4-(2-Amino-5-bromo-pyridin-3-Yl)-2-methyl-but-3-yn-2-Ol.

| | In a 1000 mL double-jacket reactor (under a nitrogen atmosphere) |
|---|---|
| 84.0 g | 2-amino-5-bromo-3-iodopyridine (96.4% (m/m)) is suspended in |
| 900 g | dichloromethane. The suspension is heated to reflux (45° C. jacket temperature) and stirred at slightly reflux for 15 to 45 minutes. The dimmished solution is cooled to 30 to 35° C. and then polish-filtered (using a Zeta plus filter plate charged with Decalite Speedex). The first reactor and the transfer pipe are rinsed with |
| 130 g | dichloromethane (pre-heated to 30 to 35° C.). The clear filtrate is concentrated to a residual volume of 260 to 300 mL. The resulting suspension is treated at ca. 30° C. with |
| 600 mg | bis-(triphenylphosphine)-palladium(II)-dichloride, |
| 400 mg | copper(I)-iodide and |

| | In a 1000 mL double-jacket reactor (under a nitrogen atmosphere) |
|---|---|
| 38.0 g | triethylamine. The used receivers are rinsed with |
| 10 g | dichloromethane. The brown suspension is treated at 30 to 34° C. within 1 to 2 hours with a solution of |
| 32.0 g | 2-methyl-3-butin-2-ol in |
| 120 g | dichloromethane. The dropping funnel is rinsed with |
| 15 g | dichloromethane. The mixture is stirred for 10 hours at 30 to 34° C. In-process control. Upon complete conversion the mixture is diluted at 30 to 34° C. with |
| 240 g | dichloromethane and |
| 200 g | water and treated at 28 to 34° C. within 10 to 20 minutes with |
| 100 g | ammonium hydroxide solution (25% in water). The biphasic solution (ca. 950 mL) is stirred for 15 to 30 minutes at 28 to 34° C. and the layers are then allowed to separate for 15 to 30 minutes. The organic layer is separated and the aqueous layer is extracted at 28 to 34° C. with |
| 80 g | dichloromethane. The combined organic layers are diluted at 30 to 34° C. with |
| 100 g | water and then treated at 28 to 34° C. within 10 to 20 minutes with |
| 50 g | ammonium hydroxide solution (25% in water). The biphasic solution is stirred for 15 to 30 minutes at 28 to 34° C. and the layers are then allowed to separate for 15 to 30 minutes. The organic layer is separated and then washed at 28 to 34° C. with |
| 100 g | water. The organic layer is concentrated under reduced pressure and at a maximum temperature of 34° C. to a volume of 550 to 600 mL. The organic layer is diluted at 25 to 32° C. with |
| 400 g | water and treated at 25 to 32° C. within 15 to 30 minutes with |
| 45 g | hydrochloric acid (37% in water). The biphasic solution (980 mL) is stirred for 15 to 30 minutes at 25 to 32° C. and the layers are then allowed to separate for 30 to 60 minutes. The layers are separated and the organic layer is diluted with |
| 225 g | water and then treated at 25 to 32° C. within 15 to 30 minutes with |
| 25 g | hydrochloric acid (37% in water). The combined product containing aqueous layers are washed at 25 to 32° C. with |
| 100 g | dichloromethane. From the aqueous layer dichloromethane is then azeotropically removed with water under reduced pressure and at a maximum internal temperature of 32° C. At the end of the distillation a volume of 550 to 600 mL is adjusted. The resulting aqueous solution is polish-filtered (using a Zeta plus filter plate). The first reactor and the transfer pipes are rinsed with |
| 40 g | water. The clear solution is then treated at 22 to 30° C. within 60 to 120 minutes with approximately |
| 54 g | sodium hydroxide (28% in water) until the pH is adjusted to pH 7.5 to 9.5. This forces the product to precipitate. After the dosing the resulting suspension is stirred at 20 to 25° C. for 4 to 16 hours. The crystals are filtered off and washed in two portions with |
| 300 g | water. The wet crystals (ca. 73 g) are dried at 40 to 50° C. and <30 mbar until constant weight. |

Yield: 65.04 g (93%) of yellow crystals with a content of 98.6% (m/m).
This intermediate can optionally be re-crystallized from isopropanol/water for further purification.

$^1$H NMR (400 MHz, CDCl$_3$): δ ppm 1.61 (s, 6H); 2.3 (br., 1H); 4.9 (br., 2H); 7.57 (d, J=2.4, 1H); 8.01 (d, J=2.4, 1H).

Example 7 a) Preparation of 5-bromo-7-azaindole (3 or Ia) from isolated 2-amino-5-bromo-3-iodopyridine

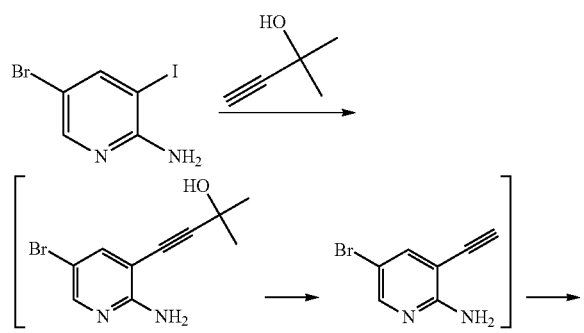

-continued

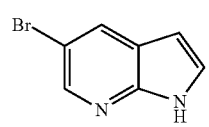

A suspension of 2-amino-5-bromo-3-iodopyridine (5.0 g, 16.7 mmol), bis-(triphenyl-phosphine)-palladium(II)-dichloride (43 mg, 0.061 mmol), copper(I)iodide (29.4 mg, 0.15 mmol) and triethylamine (2.21 g, 21.8 mmol) in dichloromethane (20 mL) was treated at 23 to 30° C. within 1 to 2 hours with a solution of 1,1-dimethyl-2-propyn-1-ol (1.85 g, 21.7 mmol) in dichloromethane (10 mL) and the resulting mixture was stirred at 25° C. for 4 hours. The mixture was diluted with dichloromethane (10 mL) and washed with water (2×25 mL). The organic phase was then treated with 1 M HCl (40 mL). The layers were separated and the organic layer was extracted with 1 M HCl (15 mL). The combined product containing aqueous layers were washed with dichloromethane (2×8 mL). The pH of the aqueous layer was adjusted to pH 7-9 by the drop wise addition of sodium hydroxide solution (28% in water). The resulting suspension was stirred at 20° C. over night and the crystals were then filtered off and washed with water (2×5 mL). The wet crystals were dissolved in N-methylpyrrolidone (50 mL) and treated within 2 hours at 60° C. and 50-100 mbar with an aqueous solution of lithium hydroxide (2.4 M, 32 mL). The resulting mixture was heated to 75° C. and stirred at this temperature and under reduced pressure (50-100 mbar) for 15-20 hours. Toluene (20 mL) and water (20 mL) were then added and the layers were separated. The aqueous layer was extracted with toluene (3×25 mL). The combined organic layers were washed with water (3×10 mL) and then concentrated to dryness. The residue was dissolved in N-methylpyrrolidone (50 mL) and treated at 60° C. with potassium tert.-butylate (3.52 g, 30.7 mmol). After stirring for 3 hours at 60° C., the mixture was cooled to ambient temperature and diluted with toluene (40 mL) and water (40 mL). The aqueous layer was separated and back extracted with toluene (3×50 mL). The combined toluene layers were washed with water (3×10 mL) and then concentrated to dryness. The residue was dissolved in a hot mixture of toluene and n-heptane (20 mL). The clear solution was cooled to −5° C. within 4 to 6 hours whereupon crystals precipitated. The suspension was stirred at −5° C. for 2-4 hours. The crystals were filtered off, washed with heptane and dried at 45° C./<30 mbars over night to afford 5-bromo-7-azaindole (2.05 g, 62% yield) as slightly yellow crystals with a purity of 99.6% (HPLC, area%).

b) Preparation of 5-bromo-7-azaindole from isolated 4-(2-Amino-5-bromo-pyridin-3-yl)-2-methyl-but-3-yn-2-ol.

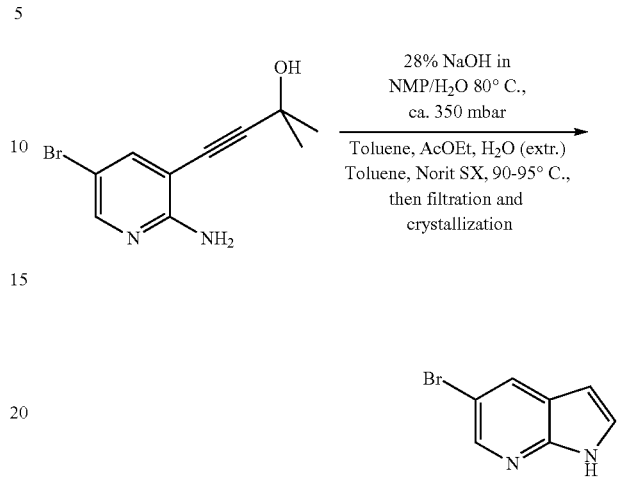

A 1000 mL double-jacket reactor (under a nitrogen atmosphere) is charged with

| | | |
|---|---|---|
| 80.0 | g | 4-(2-amino-5-bromo-pyridin-3-yl)-2-methyl-but-3-yn-2-ol, |
| 320 | mL | N-methylpyrrolidone and |
| 330 | mL | water. The mixture is heated to 75 to 80° C. and a vacuum of ca 350 mbar is applied. The solution is then treated at 75 to 80° C. within 30 to 45 minutes with |
| 181 | mL | sodium hydroxide (28% in water). The dropping funnel is rinsed with |
| 5 | mL | water and the mixture stirred at 78 to 81° C. for 15 to 20 hours. During stirring the jacket temperature and the vacuum have to be adjusted such that the internal temperature is 78 to 81° C. and a slight steadily distillate flow is guaranteed. When the volume in the reactor has reached approx. 800 mL water is continuously added to keep the volume constant for the rest of the reaction time. In-process control. Upon complete conversion, the reaction mixture is concentrated to a volume of approx. 700 mL and then cooled to 50 to 55° C. The mixture is treated at this temperature with |
| 200 | mL | toluene. The biphasic mixture (ca. 900 mL) is stirred at 50 to 55° C. for 15 to 30 minutes and the layers are then allowed to separate for 15 to 30 minutes. The aqueous layer is separated and then extracted at 50 to 55° C. with 3 × 140 mL, totally with |
| 420 | mL | toluene. The combined toluene layers are washed at 50 to 55° C. with 2 × 100 mL, totally with |
| 200 | mL | water. The toluene layer is concentrated under reduced pressure at 45 to 55° C. until a residual volume of 450 to 500 mL is obtained. The residue is treated at 50 to 55° C. with |
| 225 | g | ethyl acetate and the resulting solution is washed at 50 to 55° C. with 3 × 150 mL, totally with |
| 450 | mL | water. From the organic layer, water and ethyl acetate are azeotropically distilled off with toluene under reduced pressure at 45 to 55° C. At the end of the distillation a volume of 600 to 700 mL is adjusted. The mixture is heated to 90 to 95° C. and stirred until a clear solution is obtained. The solution is treated with |
| 2.0 | g | activated charcoal (Norit SX) and the resulting mixture stirred for 15 to 30 minutes at 90 to 95° C. The charcoal is removed by a hot filtration at 90 to 95° C. The first reactor, the filter and the transfer pipes are washed with 3 × 100 mL, totally with |
| 300 | mL | toluene. The filtrate is concentrated under reduced pressure to a volume of approx. 400 mL. The resulting suspension is heated to 90 to 100° C. to obtain a clear solution. The solution is cooled to −5 to −10° C. within 7 to 10 hours and the resulting suspension stirred at this temperature for additional 3 to 5 hours. The crystals are filtered off and washed in two portions with |
| 120 | mL | toluene (pre-cooled to <0° C.). The wet crystals are dried at 55 to 65° C./<30 mbar until constant weight. |

Yield: 46.5 g (75%) of slightly yellow crystals with an assay of 100.1% (m/m).

Example 8

Preparation of 5-Chloro-7-Azaindol (Ib)

Step 1: Synthesis of 2-Amino-5-chloro-3-iodopyridine (IIb)

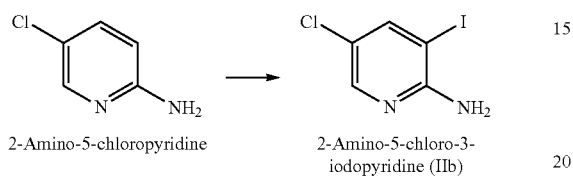

2-Amino-5-chloropyridine → 2-Amino-5-chloro-3-iodopyridine (IIb)

| In a 1000 mL double-jacket reactor under a nitrogen atmosphere | |
|---|---|
| 38.28 g | iodine is suspended in |
| 21 g | acetic acid and |
| 62 g | acetonitrile. To the brown mixture is added at 20 to 40° C. |
| 14.6 g | sulfuric acid 96%. The addition is strongly exothermic. The dropping funnel is rinsed with |
| 20 g | water. The resulting mixture is heated with a jacket temperature of 90° C. When the temperature of the mixture is 70° C., the mixture is treated within 3 to 6 minutes with |
| 45.20 g | periodic acid (50% in water). The addition is endothermic. The funnel is rinsed with |
| 10 g | water. The solution is then treated at 65 to 75° C. within 5 to 10 minutes with a previously prepared solution of |
| 43.1 g | 2-amino-5-chloropyridine in |
| 67 g | acetonitrile and |
| 31.5 g | acetic acid. The dropping funnel is rinsed with |
| 15 g | acetonitrile. The resulting solution is heated to 77 to 82° C. and stirred under slightly reflux conditions for 4 hours (approx. 90° C. jacket temperature). The mixture is then cooled 60-65° C. and treated with |
| 66 g | sodium hydrogen sulfite (39% in water). After the addition, the mixture is diluted at 60 to 70° C. within 10 to 20 minutes with |
| 360 g | water. The mixture is then treated with |
| 162 mL | sodium hydroxide 28% to adjust the pH to pH 7.4 and the resulting suspension is stirred at 50° C. for 30 to 60 minutes. The suspension is cooled to 20 to 25° C. within 2 hours and then stirred at this temperature over night. The crystals are filtered off and washed in two portions with a mixture of |
| 270 g | water and |
| 23 g | acetonitrile. The wet crystals (approx. 110 g) are dried at 40-50° C./<30 mbar to afford 72.5 g (85%) of slightly brownish crystals with a purity of 94.8 % (area). |

Step 2: Synthesis of 4-(2-Amino-5-chloro-pyridin-3-yl)-2-methyl-but-3-yn-2-ol

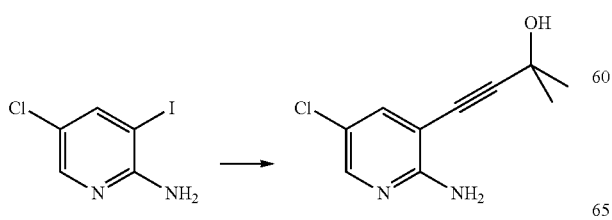

| | In a 1000 mL double-jacket reactor |
|---|---|
| 38.0 g | 2-amino-5-chloro-3-iodopyridine is suspended in |
| 120 mL | dichloromethane. The suspension is treated at ca 30° C. with |
| 0.60 g | bis-(triphenylphosphine)-palladium(II)-dichloride, |
| 0.41 g | copper(I)-iodide and |
| 27.5 mL | triethylamine. The used receivers are rinsed with |
| 10 g | dichloromethane. The brown suspension is treated at 30 to 34° C. within 1 to 2 hours with a solution of |
| 16.8 g | 2-methyl-3-butin-2-ol in |
| 60 mL | dichloromethane. The dropping funnel is rinsed with |
| 5 mL | dichloromethane. The mixture is stirred for 3 hours at 30 to 34° C. and then treated at 30 to 34° C. with |
| 100 mL | dichloromethane and |
| 150 mL | ammonium hydroxide solution (10% in water). The biphasic solution is stirred for 10 to 20 minutes at 30 to 34° C. and the layers are then allowed to separate for 15 to 45 minutes. The organic layer is separated and the aqueous layer is extracted at 30 to 34° C. with |
| 40 mL | dichloromethane. The combined organic layers are washed at 28 to 34° C. with |
| 150 mL | ammonium hydroxide solution (10% in water) and then with |
| 150 mL | water. The organic layer is then treated at 25 to 32° C. with |
| 300 mL | hydrochloric acid (1.0M in water). The biphasic solution is stirred for 20 to 30 minutes at 25 to 32° C. and the layers are then allowed to separate for 30 to 60 minutes. The organic layer is separated and extracted at 25 to 32° C. with |
| 100 mL | hydrochloric acid (1.0M in water). The combined product containing aqueous layers are washed at 25 to 32° C. with |
| 100 mL | dichloromethane. From the aqueous layer dichloromethane is then azeotropically removed with water under reduced pressure and at a maximum internal temperature of 30° C. The aqueous solution is then treated at 22 to 30° C. within 60 to 120 minutes with approximately |
| 32 mL | sodium hydroxide (28% in water) until the pH is adjusted to pH 9. This forces the product to precipitate. After the dosing the resulting suspension is stirred at 20 to 25° C. over night. The crystals are filtered off and washed in two portions with |
| 150 g | water. The wet crystals (40.2 g) are dried at 40 to 50° C. and <30 mbar until constant weight to afford 29.2 g (92%) of slightly brownish crystals with a purity of 98.7% (area). |

Step 3: Synthesis of 5-chloro-7-azaindol (Ib)

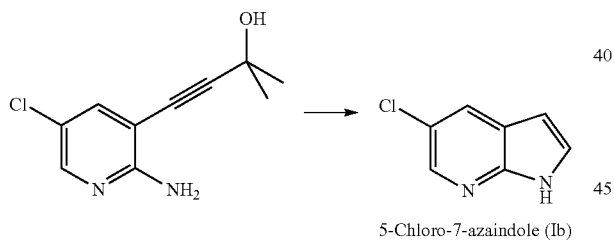

5-Chloro-7-azaindole (Ib)

| | A 500 mL double-jacket reactor (under a nitrogen atmosphere) is charged with |
|---|---|
| 25.0 g | 4-(2-amino-5-chloro-pyridin-3-yl)-2-methyl-but-3-yn-2-ol, |
| 120 mL | N-methylpyrrolidone and |
| 130 mL | water. The mixture is heated to 75 to 80° C. (ca. 95° C. jacket temperature) and a vacuum of ca. 350 mbar is applied. The solution is then treated at 75 to 80° C. within 30 to 45 minutes with |
| 85 mL | sodium hydroxide (28% in water). The dropping funnel is rinsed with |
| 5 mL | water and the mixture stirred at 78 to 81° C. over night. During stirring the jacket temperature and the vacuum have to be adjusted such that a slight steadily distillate flow is guaranteed. In a typical lab experiment approx. 50 mL of water/acetone are distilled off in 2 hours. During the reaction, water is continuously added to keep the volume constant at approx. 270 mL. Upon complete conversion, the reaction mixture is cooled to 50 to 55° C. The mixture is treated at this temperature with |
| 60 mL | toluene. The biphasic mixture is stirred at 50 to 55° C. for 15 to 30 minutes and the layers are then allowed to separate for 15 to 30 minutes. The aqueous layer is separated and then extracted at 50 to 55° C. with 3 × 50 mL with |

-continued

| A 500 mL double-jacket reactor (under a nitrogen atmosphere) is charged with |
|---|
| toluene. The combined toluene layers are washed at 50 to 55° C. with 5 × 40 mL with water. The toluene layer is concentrated to dryness. The residue (17.3 g) is crystallized from 90 mL toluene to afford 13.0 g (71%) of 5 chloro-7-azaindol (Ib) as slightly yellow crystals with a purity of 96.7% (area). |

The invention claimed is:

1. A composition comprising compound (B),

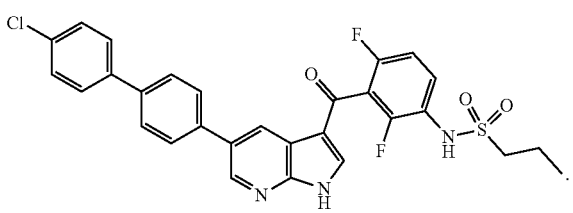

(B)

2. The composition according to claim 1, wherein said compound (B) is present in an amount of less than 0.30% by weight of the composition.

3. The composition according to claim 1, wherein said compound (B) is present in an amount of from about 0.01% to about 0.15% by weight of the composition.

4. The composition according to claim 1, wherein said compound (B) is present in an amount of from about 0.02% to about 0.15% by weight of the composition.

5. The composition according to claim 1, wherein said compound (B) in the composition is detectable by high performance liquid chromatography, mass spectrometry, proton nuclear magnetic resonance spectroscopy, infrared spectroscopy, or a combination thereof.

6. The composition according to claim 5, wherein said compound (B) in the composition is detectable by high performance liquid chromatography.

7. The composition according to claim 5, wherein said compound (B) in the composition is detectable by high performance liquid chromatography in combination with mass spectrometry.

8. The composition according to claim 2, wherein said compound (B) in the composition is detectable by high performance liquid chromatography, mass spectrometry, proton nuclear magnetic resonance spectroscopy, infrared spectroscopy, or a combination thereof.

9. The composition according to claim 8, wherein said compound (B) in the composition is detectable by high performance liquid chromatography.

10. The composition according to claim 8, wherein said compound (B) in the composition is detectable by high performance liquid chromatography in combination with mass spectrometry.

11. The composition according to claim 3, wherein said compound (B) in the composition is detectable by high performance liquid chromatography, mass spectrometry, proton nuclear magnetic resonance spectroscopy, infrared spectroscopy, or a combination thereof.

12. The composition according to claim 11, wherein said compound (B) in the composition is detectable by high performance liquid chromatography.

13. The composition according to claim 11, wherein said compound (B) in the composition is detectable by high performance liquid chromatography in combination with mass spectrometry.

14. The composition according to claim 4, wherein said compound (B) in the composition is detectable by high performance liquid chromatography, mass spectrometry, proton nuclear magnetic resonance spectroscopy, infrared spectroscopy, or a combination thereof.

15. The composition according to claim 14, wherein said compound (B) in the composition is detectable by high performance liquid chromatography.

16. The composition according to claim 14, wherein said compound (B) in the composition is detectable by high performance liquid chromatography in combination with mass spectrometry.

17. A composition comprising compound (B):

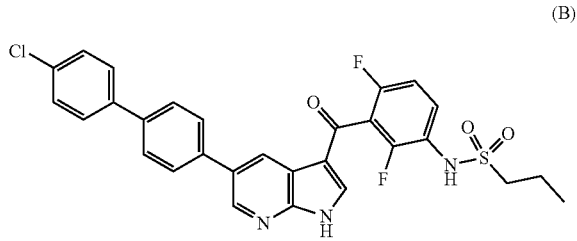 [SMILES: CCCS(=O)(=O)Nc1ccc(F)c(C(=O)c2c[nH]c3ncc(-c4ccc(-c5ccc(Cl)cc5)cc4)cc23)c1F]

(B)

and propane-1-sulfonic acid {3-[5-(4-chloro-phenyl)-1H-pyrrolo[2,3-b]pyridine-3-carbonyl]-2,4-difluoro-phenyl}-amide.

18. The composition according to claim 17, wherein said compound (B) is present in an amount of less than 0.30% by weight of the composition.

19. The composition according to claim 17, wherein said compound (B) is present in an amount of from about 0.01% to about 0.15% by weight of the composition.

20. The composition according to claim 17, wherein said compound (B) is present in an amount of from about 0.2% to about 0.15% by weight of the composition.

21. The composition according to claim 17, wherein said propane-1-sulfonic acid {3-[5-(4-chloro-phenyl)-1H-pyrrolo[2,3-b]pyridine-3-carbonyl]-2,4-difluoro-phenyl}-amide is present in an amount of greater than 99% by weight of the composition.

22. The composition according to claim 18, wherein said propane-1-sulfonic acid {3-[5-(4-chloro-phenyl)-1H-pyrrolo[2,3-b]pyridine-3-carbonyl]-2,4-difluoro-phenyl}-amide is present in an amount of greater than 99% by weight of the composition.

23. The composition according to claim 19, wherein said propane-1-sulfonic acid {3-[5-(4-chloro-phenyl)-1H-pyrrolo[2,3-b]pyridine-3-carbonyl]-2,4-difluoro-phenyl}-amide is present in an amount of greater than 99% by weight of the composition.

24. The composition according to claim 20, wherein said propane-1-sulfonic acid {3-[5-(4-chloro-phenyl)-1H-pyrrolo[2,3-b]pyridine-3-carbonyl]-2,4-difluoro-phenyl}-amide is present in an amount of greater than 99% by weight of the composition.

25. A composition comprising:

(a) a mixture of compound (B):

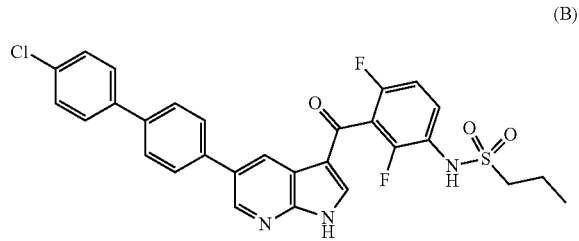 [SMILES: CCCS(=O)(=O)Nc1ccc(F)c(C(=O)c2c[nH]c3ncc(-c4ccc(-c5ccc(Cl)cc5)cc4)cc23)c1F]

and propane-1-sulfonic acid {3-[5-(4-chloro-phenyl)-1H-pyrrolo[2,3-b]pyridine-3-carbonyl]-2,4-difluoro-phenyl}-amide; and (b) a pharmaceutically acceptable excipient.

26. The composition according to claim 25, wherein said compound (B) is present in an amount of less than 0.30% by weight of the mixture.

27. The composition according to claim 25, wherein said compound (B) is present in an amount of from about 0.01% to about 0.15% by weight of the mixture.

28. The composition according to claim 25, wherein said compound (B) is present in an amount of from about 0.02% to about 0.15% by weight of the mixture.

29. A composition comprising compound (B):

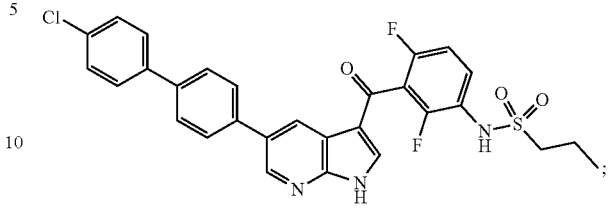

and a pharmaceutically acceptable excipient.

30. The composition according to claim 29, wherein said compound (B) is present in an amount of less than 0.30% by weight of the composition.

31. The composition according to claim 29, wherein said compound (B) is present in an amount of from about 0.01% to about 0.15% by weight of the composition.

32. The composition according to claim 29, wherein said compound (B) is present in an amount of from about 0.02% to about 0.15% by weight of the composition.

33. The composition according to claim 29, wherein said compound (B) in the composition is detectable by high performance liquid chromatography, mass spectrometry, proton nuclear magnetic resonance spectroscopy, infrared spectroscopy, or a combination thereof.

34. The composition according to claim 33, wherein said compound (B) in the composition is detectable by high performance liquid chromatography.

35. The composition according to claim 33, wherein said compound (B) in the composition is detectable by high performance liquid chromatography in combination with mass spectrometry.

36. A compound that is compound (B):

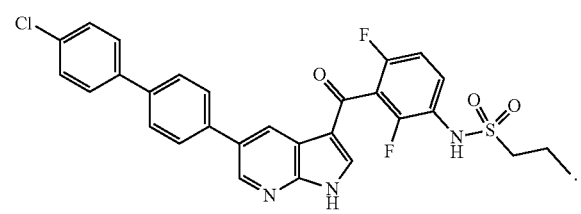

* * * * *